(12) United States Patent
Thackeray et al.

(10) Patent No.: US 8,900,792 B2
(45) Date of Patent: Dec. 2, 2014

(54) POLYMERIZABLE PHOTOACID GENERATORS

(75) Inventors: James W. Thackeray, Braintree, MA (US); Suzanne M. Coley, Mansfield, MA (US); Vipul Jain, Westborough, MA (US); Owendi Ongayi, Marlborough, MA (US); James F. Cameron, Brookline, MA (US); Paul J. Labeaume, Framingham, MA (US); Ahmad E. Madkour, Midland, MI (US)

(73) Assignees: Rohm and Haas Electronic Materials LLC, Marborough, MA (US); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/339,948

(22) Filed: Dec. 29, 2011

(65) Prior Publication Data
US 2012/0171616 A1    Jul. 5, 2012

Related U.S. Application Data

(60) Provisional application No. 61/429,009, filed on Dec. 31, 2010.

(51) Int. Cl.
| G03F 7/004 | (2006.01) |
| G03F 7/029 | (2006.01) |
| C07D 333/76 | (2006.01) |
| G03F 7/20 | (2006.01) |
| C07C 309/12 | (2006.01) |
| C07C 309/42 | (2006.01) |
| C07C 381/12 | (2006.01) |
| G03F 7/039 | (2006.01) |
| C08F 220/38 | (2006.01) |

(52) U.S. Cl.
CPC .............. *G03F 7/0045* (2013.01); *G03F 7/20* (2013.01); *C07C 309/12* (2013.01); *C07C 309/42* (2013.01); *C07C 381/12* (2013.01); *G03F 7/0046* (2013.01); *G03F 7/0397* (2013.01); *C07D 333/76* (2013.01); *C08F 220/38* (2013.01); *Y10S 430/122* (2013.01); *Y10S 430/123* (2013.01); *Y10S 430/126* (2013.01)
USPC ........ 430/270.1; 430/326; 430/921; 430/922; 430/925; 526/245; 526/318; 526/326

(58) Field of Classification Search
USPC .............. 430/270.1, 326, 913, 914, 921, 922, 430/925, 942; 522/7–49; 526/245, 319, 526/326; 562/30
See application file for complete search history.

(56) References Cited

U.S. PATENT DOCUMENTS

| 2,964,557 | A | 12/1960 | Niederhauser et al. |
| 3,759,985 | A | 9/1973 | Nukina et al. |
| 5,945,250 | A | 8/1999 | Aoai et al. |
| 7,776,510 | B2 | 8/2010 | Iwai et al. |
| 7,833,690 | B2 | 11/2010 | Gonsalves et al. |
| 2009/0202943 | A1 | 8/2009 | Ohsawa et al. |
| 2009/0269696 | A1* | 10/2009 | Ohsawa et al. ............. 430/270.1 |
| 2009/0288855 | A1* | 11/2009 | Nishikawa et al. ........ 174/126.1 |
| 2010/0040977 | A1 | 2/2010 | Nagai et al. |
| 2010/0063232 | A1 | 3/2010 | Nagai et al. |
| 2010/0183975 | A1* | 7/2010 | Takahashi et al. ......... 430/270.1 |
| 2011/0015431 | A1 | 1/2011 | Jodry et al. |
| 2011/0177453 | A1 | 7/2011 | Masubuchi et al. |
| 2011/0244392 | A1* | 10/2011 | Hirano et al. .............. 430/270.1 |
| 2012/0171616 | A1 | 7/2012 | Thackeray et al. |

FOREIGN PATENT DOCUMENTS

| EP | 2020616 | A2 | 2/2009 |
| EP | 2080774 | A1 | 7/2009 |
| EP | 2088467 | A1 | 8/2009 |
| EP | 2090931 | A1 | 8/2009 |
| EP | 2341089 | A1 | 7/2011 |
| JP | 2006219419 | A | 8/2009 |
| JP | 2010024215 | A | 2/2010 |
| JP | 2010044253 | A | 2/2010 |
| WO | WO 2008/056795 | * | 5/2008 |
| WO | 2009019793 | A1 | 2/2009 |

(Continued)

OTHER PUBLICATIONS

U.S. Appl. No. 13/339,831, filed Dec. 29, 2011.

(Continued)

*Primary Examiner* — Anca Eoff
(74) *Attorney, Agent, or Firm* — Cantor Colburn LLP

(57) ABSTRACT

A compound has formula (I):

Q-O-(A)-Z⁻G⁺    (I)

wherein Q is a halogenated or non-halogenated, $C_{2-30}$ olefin-containing group, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, Z is an anionic group comprising sulfonate, sulfonamide, or sulfonimide, and G⁺ has formula (II):

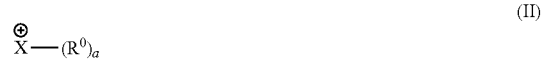

wherein X is S or I, each $R^0$ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination of these, wherein when X is S, one of the $R^0$ groups is optionally attached to one adjacent $R^0$ group by a single bond, and a is 2 or 3, wherein when X is I, a is 2, or when X is S, a is 3. A copolymer, a photoresist, a coated substrate and method of patterning are disclosed.

10 Claims, No Drawings

(56) References Cited

FOREIGN PATENT DOCUMENTS

| WO | 2009152276 A2 | | 12/2009 |
|---|---|---|---|
| WO | 2010026973 A1 | | 3/2010 |
| WO | WO 2010/044372 | * | 4/2010 |

OTHER PUBLICATIONS

U.S. Appl. No. 13/340,088, filed Dec. 29, 2011.
International Publication No. 2009019793 (A1); Publication Date: Feb. 12, 2009; Abstract Only, 2 pages.
European Search Report dated Dec. 14, 2012; Application No. 11195707.2; 4 pages.
JP2006178317A; Jul. 6, 2006; Machine Translation; 100 pages.
Benrabah et al., "Perfluorosulfonate-Polyether Based Single Ion Conductors", Electrochimica Acta, 40(13-14), 1995, pp. 2259-2264.
Ritter et al., "Synthesis and characterization of thiophenes with fluorinated substituents", Journal of Fluorine Chemistry, 93, 1999, pp. 73-79.
CN 101687740 A; Date of Publication Mar. 31, 2010; English Abstract; 2 pages.
CN 101799629 A; Date of Publication Aug. 11, 2010; English Abstract; 2 pages.
European Search Report; European Application No. 11195705.6; Date of Mailing; May 12, 2012; Date Received: May 21, 2012, 3 pages.
JP 2006219419 A; Date of Publication Aug. 24, 2006; English Abstract; 1 page.
WO 2009037980 A1; Date of Publication Mar. 26, 2009; English Abstract; 2 pages.
JP 2010024215 A; Date of Publication Feb. 4, 2010; English Abstract; 2 pages.
Lee, C.T. et al. "The effect of direct PAG incoproation into the polymer main chain on reactive ion etch resistance of 193 nm and EUV chemically amplified resists." Microelectronic Engineering:2008. pp. 963-965. vol. 85.
Li-Qing Hu et al. "Synthesis of Perhaloalkanesulfonyl Halides and Their Sulfonimide Derivatives." Inorg. Chem. 1993. pp. 5007-5010. vol. 32.
Prakash, G.K. et al. "Preparation of x, x-difluoroalkanesulfonic acids." Journal of Fluorine Chemistry: 2004. pp. 595-601. vol. 125.
Huang et al., Inorg. Chem., 1991, 30, 789-794.
Non-Final Office Action for U.S. Appl. No. 13/340,088, Application Filing Date Dec. 29, 2011; Notification Date Sep. 3, 2013, 60 pages.

* cited by examiner

POLYMERIZABLE PHOTOACID GENERATORS

CROSS-REFERENCE TO RELATED APPLICATION

This application is a nonprovisional filing of U.S. provisional application No. 61/429,009 filed on Dec. 31, 2010, the content of which is incorporated herein by reference in its entirety.

BACKGROUND

Disclosed herein are novel photoacid generator compounds polymerizable into a photoresist polymer, and a photoresist composition which includes the polymerizable photoacid generator.

Chemical compounds which decompose to generate acids when exposed to radiation in the ultraviolet region of the spectrum (i.e., <300 nm), also known as photoacid generators, are the basis for "chemically amplified" deprotection or crosslinking of polymers in chemically amplified photoresists for microelectronics applications. Outgas sing of the decomposition products of such materials, however, can coat and corrode the optics of the exposure tools for such photoresists, where the optics may only be millimeters away from the photoresist being exposed.

While measures to limit the damaging effects of outgas sing by for example, cleaning the optics and/or including sacrificial barriers or filters have been used for earlier generation lithographic tools (operating at 248 nm and 193 nm) and using refractive optics, the industry trend toward increased resolution at smaller and smaller linewidths of less than 45 nm, and the development of new tools operating at significantly shorter wavelengths (such as in the extreme ultraviolet (EUV) region at 13.5 nm) and which use advanced reflective optics, may not be compatible with such strategies. There is therefore interest that control of outgassing should occur at the compositional level in a photoresist. In addition, control of linewidth roughness is required in advanced photoresists for use at EUV wavelengths, which correlates to the diffusability of the components of the photoresist.

European Patent No. 2 020 616 A2 discloses photoacid generators having useful outgassing characteristics, when used with a phenolic polymer having vinyl-ether derived protecting groups. The photoacid generators are based on a sulfonium cation having an aryl group connected to the sulfonium center preferably incorporating at least one hydroxy group, and a bisaryl group with each aryl commonly connected to the sulfonium center. While the photoacid generators disclosed in this reference show improved outgassing relative to, for example, triphenylsulfonium cation-based photoacid generators, the examples (particularly Examples 1 and 9) show that improvements in outgassing obtained with these photoacid generators may also compromise the linewidth roughness.

STATEMENT OF INVENTION

The above and other deficiencies of the prior art may be overcome by a compound having the formula (I):

wherein Q is a halogenated or non-halogenated, $C_{2-30}$ olefin-containing group, A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, Z is an anionic group comprising sulfonate, sulfonamide, or sulfonimide, and $G^+$ has formula (II):

wherein X is S or I, each $R^o$ is halogenated or non-halogenated and is independently $C_{1-30}$ alkyl group; a polycyclic or monocyclic $C_{3-30}$ cycloalkyl group; a polycyclic or monocyclic $C_{4-30}$ aryl group; or a combination comprising at least one of the foregoing, wherein when X is S, one of the $R^o$ groups is optionally attached to one adjacent $R^o$ group by a single bond, and a is 2 or 3, wherein when X is I, a is 2, or when X is S, a is 3.

A copolymer comprises the above compound.

A photoresist composition comprises the above copolymer.

A coated substrate comprises a substrate having one or more layers to be patterned on a surface thereof; and a layer of the above photoresist composition over the one or more layers to be patterned.

Also, a method of forming an electronic device comprises applying a layer of the above photoresist composition on a substrate; patternwise exposing the photoresist composition layer to activating radiation; and developing the exposed photoresist composition layer to provide a resist relief image.

DETAILED DESCRIPTION

Disclosed herein are novel polymerizable photoacid generators (herein, PAGs) having low outgassing properties when exposed to actinic radiation, and in particular, when used in photoresist compositions exposed to radiation for advanced lithographies, such as for e-beam, x-ray, and extreme ultraviolet (EUV) radiation having a wavelength of 13.5 nm. The photoacid generators are salts of onium cations which have high sensitivity to these actinic radiations, and which are attached to the backbone of an addition polymerized photoresist polymer through an olefinic ester polymerizable group. The decomposition products of these PAGs are reduced relative to conventional PAGs having, for example, diphenyliodonium or triphenylsulfonium cations, under similar conditions of photoresist composition, exposure, and processing.

As used herein "onium" refers to iodonium or sulfonium cations. Also as used herein, "substituted" means including a substituent such as a halogen (i.e., F, Cl, Br, I), hydroxy, amino, thiol, carboxyl, carboxylate, amide, nitrile, thiol, sulfide, disulfide, nitro, a $C_{1-10}$ alkyl, a $C_{1-10}$ alkoxy, a $C_{6-10}$ aryl, a $C_{6-10}$ aryloxy, a $C_{7-10}$ alkyl aryl, a $C_{7-10}$ alkyl aryloxy, or a combination comprising at least one of the foregoing. It will be understood that any group or structure disclosed with respect to the formulas herein may be so substituted unless otherwise specified, or where such substitution would significantly adversely affect the desired properties of the resulting structure. Also, "(meth)acrylate," as used herein, means either acrylate or methacrylate, and is not limited to either of these unless otherwise specified.

The PAGs have a cation-anion structure where the anion is the conjugate base of a fluorinated sulfonic acid, sulfonamide, or sulfonimide and further including a polymerizable group. The cation is an aryl-substituted onium (i.e., disubstituted iodonium or trisubstituted sulfonium) cation, where the substituent aryl groups are separate or attached to one or more adjacent aryl groups in, for example, a heterocycle structure which includes the onium, or as part of a fused aromatic ring system.

The polymer-bound photoacid generator has the formula (I):

$$Q\text{-}O\text{-}(A)\text{-}Z^-G^+ \qquad (I)$$

where, in formula (I), Q is a halogenated or non-halogenated, $C_{2-30}$ olefin-containing group. Preferably, Q includes a polymerizable olefin, or a group which is capable of reacting with a hydroxy group to form an acetal or ketal structure. Also in formula (I), A is a linking group including a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group. G is a photo-decomposable cation.

The linking group A may be any linking group which provides a suitable platform and functionality for the polymer-bound PAG. Preferably, A is an o-, m- or p-substituted —$C_6F_4$-group, an o-, m- or p-substituted —$C_6H_4$— group, an o-, m- or p-substituted —$(O(CH_2)_2)_k$—$C_6F_4$— group where k is an integer of 1 to 10, an o-, m- or p-substituted —$C_6H_4$— group, or a —$[(C(R^3)_2)_x$—$C(=O)O]_b$—$C((R^4)_2)_y(CF_2)_z$— group where $R^3$ and $R^4$ are each independently H, F, $C_{1-6}$ fluoroalkyl, or $C_{1-6}$ alkyl, b is 0 or 1, x is an integer of 1 to 10, y and z are independently integers of from 0 to 10, and the sum of y+z is at least 1.

Also in the polymer-bound PAG, Z is an anionic group including a sulfonate (—$SO_3^-$), the anion of a sulfonamide (—$SO_2(N^-)R'$ where R' is a $C_{1-10}$ alkyl or $C_{6-20}$ aryl), or the anion of a sulfonimide. Where Z is a sulfonimide, the sulfonimide may be an asymmetric sulfonimide having the general structure A—$SO_2$—$(N^-)$—$SO_2$—Y, where A is as described above, and Y is a straight chain or branched $C_{1-10}$ fluoroalkyl group. Preferably, the Y group is a $C_{1-4}$ perfluoroalkyl group, and is derived from the corresponding perfluorinated alkanesulfonic acid, such as trifluoromethanesulfonic acid or perfluorobutanesulfonic acid.

Q may be a radically polymerizable group such as a vinyl carbonyl or vinyl aromatic group. The polymer-bound PAG may be of formula (III) or (IV):

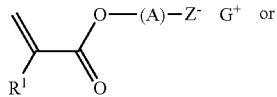

(III)

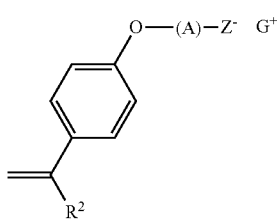

(IV)

where $R^1$ and $R^2$ are each independently H, F, $C_{1-6}$ alkyl, or $C_{1-6}$ fluoroalkyl. Also in formulas (III) and (IV), A is a fluorine-substituted $C_{1-30}$ alkylene group, a fluorine-substituted $C_{3-30}$ cycloalkylene group, a fluorine-substituted $C_{6-30}$ arylene group, or a fluorine-substituted $C_{7-30}$ alkylene-arylene group, and G is a cation of formula (II).

Exemplary polymer-bound PAGs of formula (I) include:

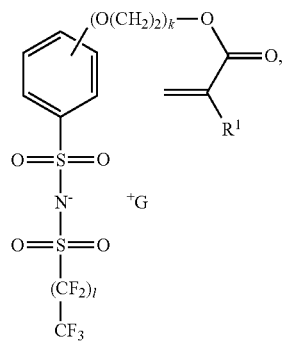

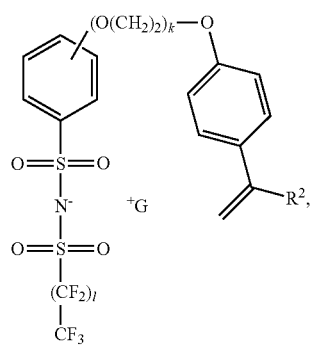

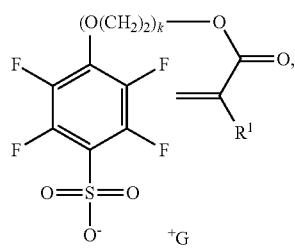

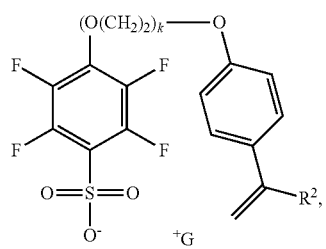

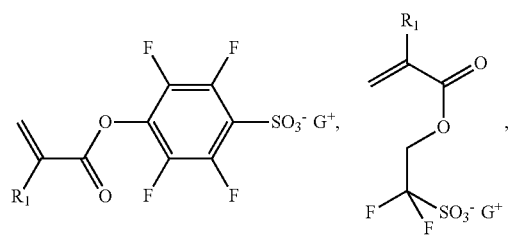

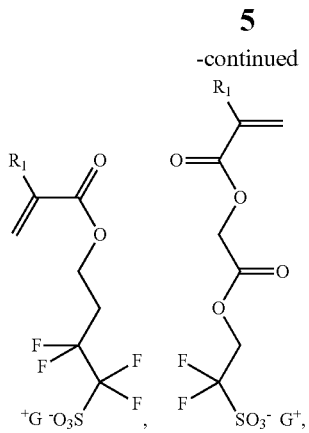

or a combination comprising at least one of the foregoing, where $R^1$ and $R^2$ are each independently H, F, $C_{1-6}$ alkyl, or $C_{1-6}$ fluoroalkyl, k is an integer of 0 to 4, 1 is an integer of 0 to 3, and G is a cation of formula (II).

$G^+$ may be an aryl-substituted onium cation of the formula (II):

wherein in formula (II), X is an onium heteroatom and is preferably S or I. Each $R^0$ is halogenated or non-halogenated and commonly attached to X, and is independently a $C_{1-30}$ alkyl group, a polycyclic or monocyclic $C_{3-30}$ cycloalkyl group, a polycyclic or monocyclic $C_{6-30}$ aryl group, or a combination comprising at least one of the foregoing.

Optionally, where X is S, one $R^0$ group of G in formula (II) may be attached to one adjacent $R^0$ group through a single bond. For example, two adjacent phenyl groups commonly attached to the sulfonium heteroatom center may be further attached to each other ortho to the point of attachment between the phenyl group and the sulfonium heteroatom (or meta, or para, or independently through different points of attachment as where one aryl is a phenyl, and the adjacent aryl is different, e.g., a naphthyl, anthracyl, etc.), by a single bond. In this way in this example, an ortho-disubstituted biphenyl fused five membered ring may be obtained, where the biphenyl is commonly connected to the sulfonium heteroatom.

Also in formula (II), a is 2 or 3, wherein when X is I, a is 2, or when X is S, a is 3. It will be further appreciated that as discussed above, the number of $R^0$ groups may refer to either independent $R^0$ groups, or may refer to one-half of an $R^0$ group attached to X where two $R^0$ groups are attached in common to each other and to X.

Preferably, G has the formula (V), (VI), or (VII):

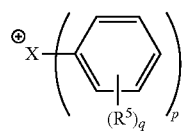

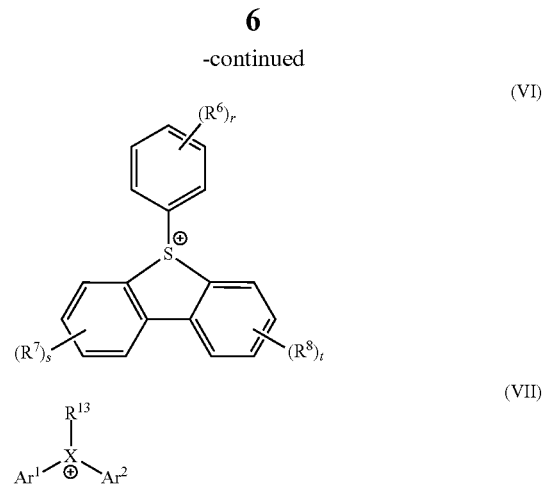

wherein X is I or S, $R^5$, $R^6$, $R^7$, and $R^8$ are each independently hydroxy, nitrile, halogen, $C_{1-10}$ alkyl, $C_{1-10}$ fluoroalkyl, $C_{1-10}$ alkoxy, $C_{1-10}$ fluoroalkoxy, $C_{6-20}$ aryl, $C_{6-20}$ fluoroaryl, $C_{6-20}$ aryloxy, or $C_{6-20}$ fluoroaryloxy, $Ar^1$ and $Ar^2$ are independently $C_{10-30}$ fused or singly bonded polycyclic aryl groups; $R^{13}$ is a lone pair of electrons where X is I, or a $C_{6-20}$ aryl group where X is S; and p is an integer of 2 or 3, wherein when X is I, p is 2, and where X is S, p is 3, q and r are each independently an integer from 0 to 5, and s and t are each independently an integer from 0 to 4.

Exemplary polymer-bound PAGs of general formula (I) include:

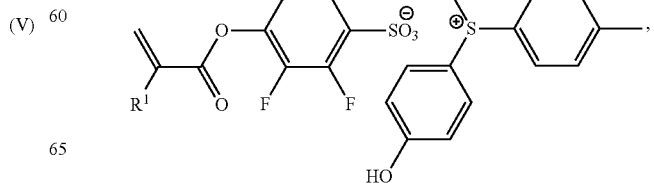

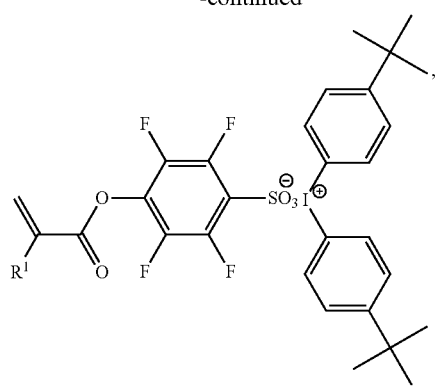
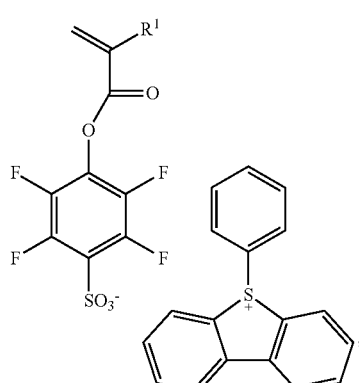
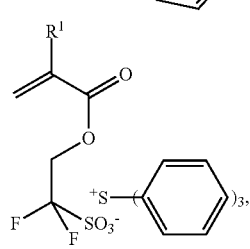
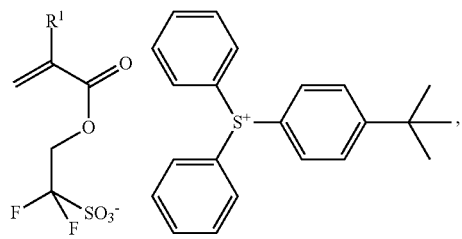
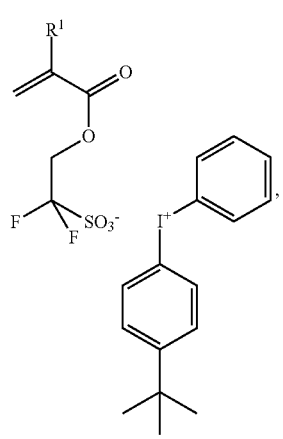
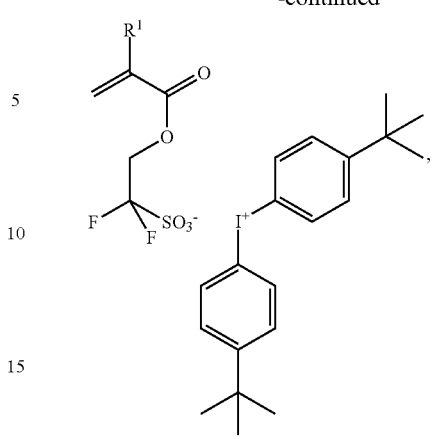
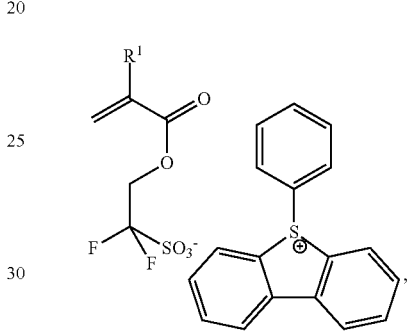
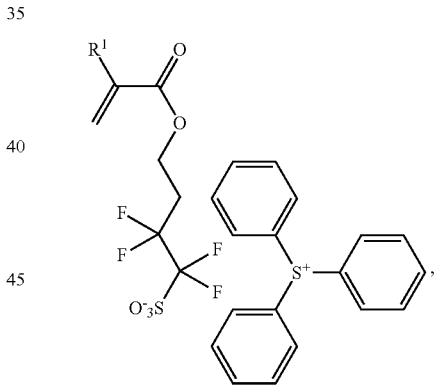
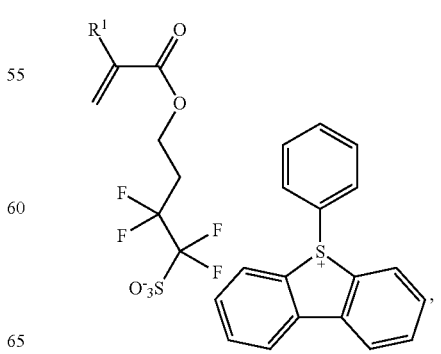

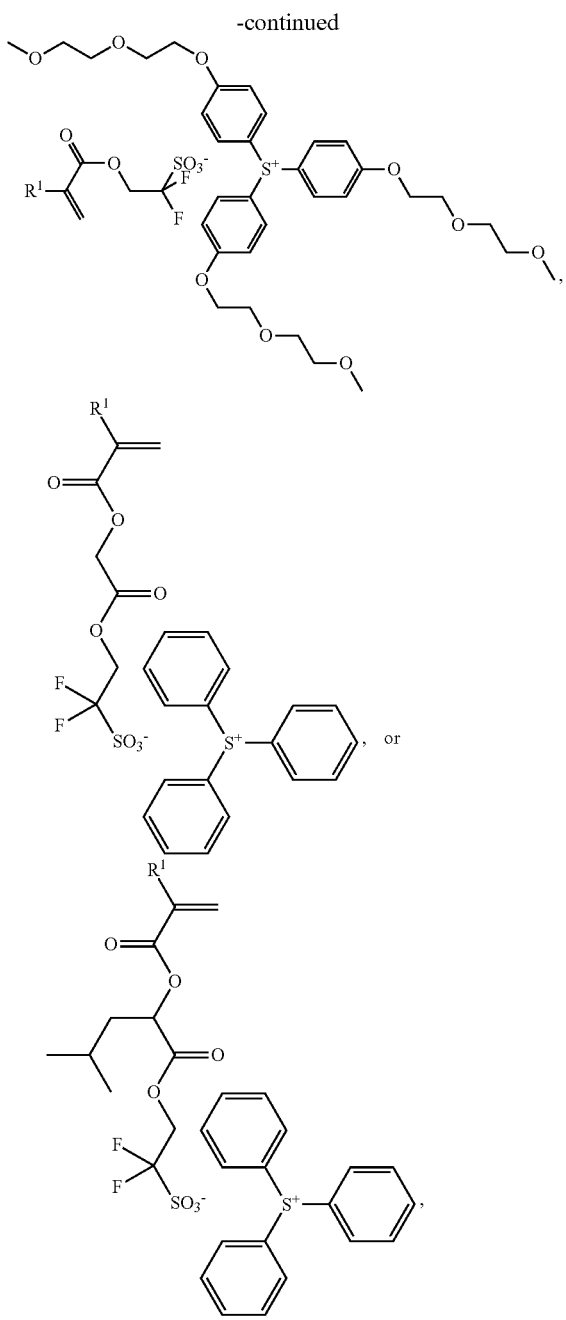

wherein $R^1$ is H, F, $C_{1-6}$ alkyl, or $C_{1-6}$ fluoroalkyl.

The PAGs disclosed herein are preferably useful in photoresists for EUV lithography, and may desirably have specific absorbance and decomposition characteristics when exposed to EUV radiation, over radiation of other wavelengths. For example, the EUV radiation source, in addition to an emission spectrum in the EUV region (about 12-14 nm, where the typical emission used is 13.4-13.5 nm) may emit at longer wavelengths to which photoacid generators may be sensitive, such as at 248 nm and/or 193 nm (which are also emission bands for KrF and ArF excimer lasers used in DUV and 193 nm lithographies). Sensitivity of the PAGs disclosed herein toward EUV is high, relative to these other emission lines, referred to in the art as "Out-of-Band" (OOB) emission wavelengths, i.e., the photospeed of the PAGs at EUV wavelengths is lower (i.e., "faster") than that of PAGs typically used at longer wavelengths (248 or 193 nm), such as triphenylsulfonium (TPS) PAGs or di-(t-butylphenyl) iodonium PAGs. The PAGs disclosed herein may preferably have an OOB sensitivity toward either 248 or 193 nm radiation, reported as a ratio of dose-to-clear ($E_0$, reported in mJ/cm$^2$) for a photoresist prepared using the PAG at EUV exposure conditions to 248 or 193 nm ($E_{0-EUV}/E_{0-248}$ or $E_{0-EUV}/E_{0-193}$) exposure conditions, of less than or equal to 2.0, specifically less than or equal to 1.5, specifically less than or equal to 1.3, more specifically less than or equal to 1.1, and still more specifically less than or equal to 1.0.

The PAGs may be prepared by a suitable general method used to prepare iodonium or sulfonium PAGs. The iodonium photoacid generators disclosed herein may generally be prepared by any of several different methods. For example, bis-aryl iodonium salts may be prepared by simple condensation of $C_{6-30}$ aryl groups substituted with electron donating groups such as, for example, alkyl groups, olefinic groups, hydroxy groups, ether groups, other aromatic groups such as phenyl groups substituted with electron donating groups (e.g. phenoxy groups), and other similar groups, with an iodate salt such as potassium iodate ($KIO_3$) under strongly acidic/dehydrating conditions (e.g., sulfuric acid and acetic anhydride) to provide the bis-aryl substituted iodonium salt precursor. Other methods useful for making both symmetric and asymmetrically substituted iodonium salt precursors in higher yield include oxidation of an aryl iodide in the presence of sodium perborate ($NaBO_3$) and acetic acid, and condensation with a second aryl iodide having an electron donating group, or with Koser's Reagent (an aryl hydroxyiodoniumtosylate, i.e., Ar—I(OH)(OTs)).

Sulfonium photoacid generators may generally be prepared by, for example, combining a sulfinyl diaryl compound (I.e., a diaryl sulfoxide prepared from $C_{6-30}$ aryl groups preferably substituted with electron donating groups as described above) with another group such as a $C_{6-30}$ aryl compound or $C_{1-30}$ alkyl group, preferably one having electron donating groups, in the presence of a suitable dehydrating agent or Lewis acid (such as, for example, sulfuric acid or Eaton's reagent) for promoting condensation of the sulfinyl group with the aryl or alkyl compound, to generate the cation. It will be appreciated that the condensation of the sulfinyl diaryl compound may also be an intramolecular condensation with a substituent group.

Iodonium or sulfonium salts prepared by any of these methods may be further subject to a metathesis anion exchange using an appropriate acid or salt of an acid, imide, or amide to provide the corresponding iodonium or sulfonium salt with the desired anion (e.g., an anion of general formula Q-O-(A)—Z, as described for formula (I)). Preferably, the anion used in the metathesis is a sulfonic acid or salt thereof, or the salt of a sulfonamide or sulfonimide.

The polymer-bound PAG compounds disclosed hereinabove are useful for preparing copolymers. The copolymer may preferably be any copolymer useful in a photoresist, without limitation; for example, polymers useful for preparing photoresists which may be used in chemically amplified positive or negative tone photoresists for DUV (248 nm) and 193 nm exposure are contemplated. More preferably, however, the copolymer is one useful for preparing photoresists for imaging with an actinic radiation for advanced microlithography, such as x-ray, e-beam, or EUV as discussed hereinabove. It will be understood that the copolymer used in this context may mean the copolymer alone, more than one copolymer, or a combination of one or more copolymers with another polymer(s) useful in a photoresist.

Preferred copolymers may include a combination of two or more polymerized units, each of which imparts a different property to the copolymer. Preferably, the copolymer includes a first polymerized unit formed from the polymer-bound PAG compound, a second polymerized unit comprising an acid sensitive functional group, and optionally a third polymerized unit comprising a polar group which is a base-soluble functional group.

In addition to the first unit comprising the polymer-bound PAG compounds discussed above, the second polymerized unit may be formed from a $C_{10-30}$ acid sensitive olefinic ester monomer having an acid-sensitive functional group. The acid-sensitive group may be a cyclic alkyl group, polycyclic alkyl group, or aromatic group, having a tertiary alkyl center to which the olefinic ester is attached.

The second polymerized unit may be formed from a compound of the formula:

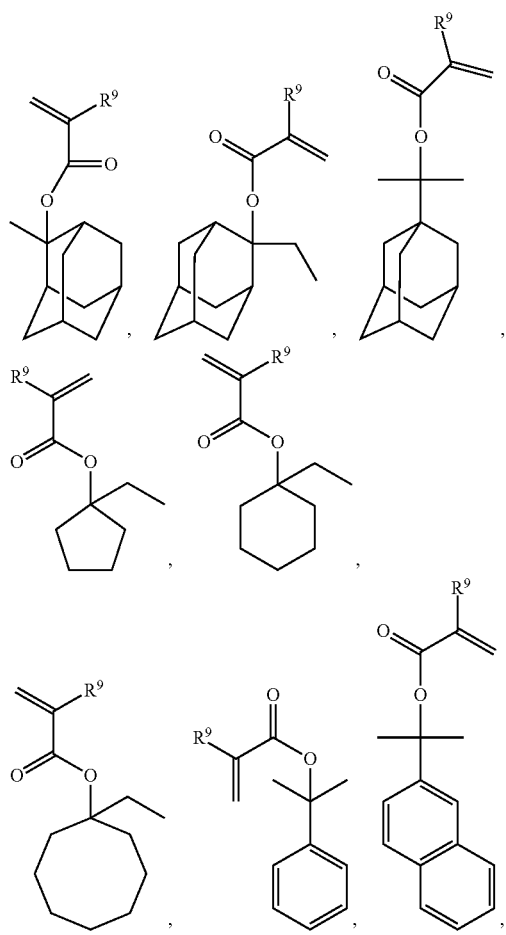

or a combination comprising at least one of the foregoing, wherein $R^9$ is H, F, $C_{1-6}$ alkyl, or $C_{1-6}$ fluoroalkyl. Preferred exemplary monomers include those in which $R^9$ in the above structures is an H or —$CH_3$ group (i.e., a (meth)acrylate group).

The third polymerized unit may be formed from a polar $C_{10-30}$ base-soluble monomer having a base-soluble functional group. The base-soluble functional group may be the olefinic ester of a cyclic alkyl group or polycyclic alkyl group having a hexafluoroisopropanol group and optionally a second polar group such as a hydroxy, or a vinyl aromatic or olefinic ester of an aromatic group having a phenolic hydroxy group or a hexafluoroisopropanol group as the base-soluble functional group.

Preferably, the third polymerized unit may be formed from a base-soluble monomer of the formula:

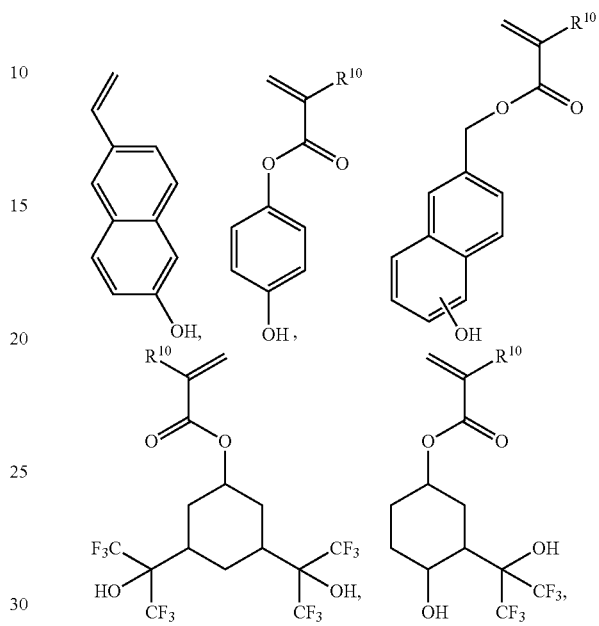

or a combination comprising at least one of the foregoing, wherein $R^{10}$ is H, F, $C_{1-6}$ alkyl, or $C_{1-6}$ fluoroalkyl. Preferred exemplary monomers include those in which $R^{10}$ in the above structures is an H or —$CH_3$ group (i.e., a (meth)acrylate group).

It will be appreciated that all copolymers containing the above-identified monomers of the first and second polymerized units are contemplated with the photoacid generators disclosed herein. It will be appreciated that additional monomeric units may further be included in the polymer, such as for example those derived from $C_{8-20}$ vinyl aromatic groups such as styrene, 4-hydroxystyrene, etc; $C_{7-20}$ cyclic olefins including norbornene and substituted norbornenes, on $C_{4-20}$ olefinic anhydrides such as maleic anhydride, itaconic anhydride, citraconic anhydride, etc.; other $C_{10-30}$ (meth)acrylate monomers including those having lactone functional groups such as, for example, alpha-(gammabutyrolactone) (meth) acrylate, and combinations including at least one of the foregoing.

A photoresist composition includes the copolymer having the polymer-bound PAG as described above. The photoresist may also include, in addition to the PAG compound and polymer, additives including for example a photo-destroyable base, and a surfactant. Other additives, such as dissolution rate inhibitors, sensitizers, additional PAGs, etc. may also be included. The photoresist components are dissolved in solvent for dispense and coating.

The photoresist may include a photo-destroyable base. Inclusion of base materials, preferably the carboxylate salts of photo-decomposable cations, provides a mechanism for neutralization of acid from the acid decomposable groups, and limits the diffusion of the photogenerated acid, to thereby provide improved contrast in the photoresist.

Photo-destroyable bases include photo-decomposable cations, and preferably those also useful for preparing PAGs, paired with an anion of a weak (pKa>2) acid such as, for example, a $C_{1-20}$ carboxylic acid. Exemplary such carboxylic acids include formic acid, acetic acid, propionic acid, tartaric acid, succinic acid, cyclohexylcarboxylic acid, benzoic acid, salicylic acid, and other such carboxylic acids. Photo-destroyable bases include cation/anion pairs of the following structures, and the cation is triphenylsulfonium or one of the following:

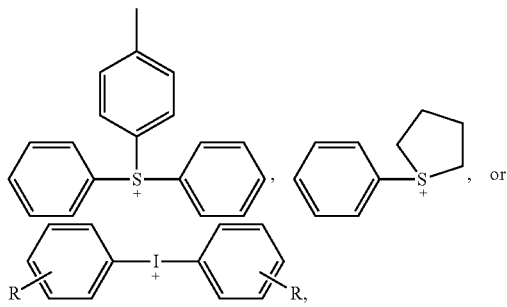

where R is independently H, a $C_{1-20}$ alkyl, a $C_{6-20}$ aryl, or a $C_{6-20}$ alkyl aryl, and the anion is

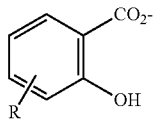

or RC(=O)—O$^-$
where R is independently H, a $C_{1-20}$ alkyl, a $C_{1-20}$ alkoxy, a $C_{6-20}$ aryl, or a $C_{6-20}$ alkyl aryl. Other photo-destroyable bases include those based on non-ionic photo-decomposing chromophores such as, for example, 2-nitrobenzyl groups and benzoin groups. An exemplary photobase generator is ortho-nitrobenzyl carbamate.

Alternatively, or in addition, other additives may include quenchers that are non-photo-destroyable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as Troger's base, a hindered amine such as diazabicycloundecene (DBU) or diazabicyclononene (DBM), or ionic quenchers including quaternary alkyl ammonium salts such as tetrabutylammonium hydroxide (TBAH) or tetrabutyl ammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

The photoresist composition disclosed herein may include the copolymer in an amount of 50 to 99 wt %, specifically 55 to 95 wt %, more specifically 60 to 90 wt %, and still more specifically 65 to 90 based on the total weight of solids. It will be understood that "copolymer" used in this context of a component in a photoresist may mean only the copolymer disclosed herein, or a combination of the copolymer with another polymer useful in a photoresist. The photo-destroyable base may be present in the photoresist in an amount of 0.01 to 5 wt %, specifically 0.1 to 4 wt %, and still more specifically 0.2 to 3 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, specifically less than or equal to 20%, or more specifically less than or equal to 10%, based on the total weight of solids. The total solids content for the photoresist composition may be 0.5 to 50 wt %, specifically 1 to 45 wt %, more specifically 2 to 40 wt %, and still more specifically 5 to 35 wt %, based on the total weight of solids and solvent. It will be understood that the solids includes copolymer, photo-destroyable base, quencher, surfactant, any added PAG, and any optional additives, exclusive of solvent.

The photoresist including the polymer-bound PAGs disclosed herein may be used to provide a layer comprising the photoresist, which produces volatile degradation products in a concentration lower than that obtained for a layer comprising a comparative photoresist comprising a polymer without the polymer-bound PAG but otherwise identical, and including non-polymer bound photoacid generator, such as for example triphenylsulfonium perfluorobutanesulfonate. When exposed to EUV radiation under identical conditions, the amount of volatile degradation products for the polymer bound PAG photoresist is lower than the comparative as determined by methods such as residual gas analysis (RGA), or film shrinkage A coated substrate may be formed from the photoresist containing the polymer-bound PAG. Such a coated substrate includes: (a) a substrate having one or more layers to be patterned on a surface thereof; and (b) a layer of the photoresist composition including the polymer-bound PAG over the one or more layers to be patterned.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 20 cm, 30 cm, or larger in diameter, or other dimensions useful for wafer fabrication production.

Further, a method of forming an electronic device includes (a) applying a layer of a photoresist composition including the polymer-bound PAG on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and baked on a hot plate to remove residual solvent and free volume from the film to make it uniformly dense.

Patternwise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the PAG in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is positive tone) or removing the unexposed portions of the film (where the photoresist is crosslinkable in the exposed regions, i.e., negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. A pattern forms by developing.

The photoresist may, when used in one or more such a pattern-forming processes, be used to fabricate electronic and optoelectronic devices such as memory devices, processor chips (CPU's), graphics chips, and other such devices.

The invention is further illustrated by the following examples. All compounds and reagents used herein are available commercially except where a procedure is provided below. Comparative PAG 1 was obtained commercially from Central Glass.

Structural characterization was carried out by nuclear magnetic resonance (NMR) spectrometry on an INOVA 500 NMR Spectrometer with OMNI-PROBE (operating at 500 MHz for proton) or GEMINI 300 NMR Spectrometer (operating at 282 MHz for fluorine), each from Varian. Polymer composition was determined by quantitative $^{13}$C NMR at 125 MHz using NOE suppression techniques (i.e., Cr(acetylacetonate)$_3$ and a pulse delay of >5 seconds). Molecular weight (Mw) and polydispersity (PD) were determined by gel permeation chromatography (GPC) using a sample concentration of 1 mg/ml and a crosslinked styrene-divinylbenzene column with universal calibration curve calibrated with polystyrene standards, and eluted with tetrahydrofuran containing 0.02 wt % LiNO$_3$ at a flow rate of 1 ml/min.

Synthesis of triphenylsulfonium 2,3,5,6-tetrafluoro-4-(methacryloyloxy)benzene sulfonate (Comparative PAG 2). Sodium 4-hydroxy-2,3,5,6-tetrafluorobenzene sulfonate (50 g, 0.1865 mol) was suspended in 400 mL of trifluoroacetic acid. Methacrylic acid (40 g, 0.4646 mol) was added and the mixture was heated to 70° C. in an oil bath. 75 mL of trifluoroacetic anhydride was added all at once, and the mixture was stirred at 70° C. for two hours. The reaction mixture was cooled a few crystals (about 12.5 mg) of hydroquinone were added to inhibit polymerization, and the solvents were removed under reduced pressure. A paste thus obtained of the crude product was dissolved in about 125 mL of acetone poured slowly into heptane. The precipitate was collected by filtration, air dried overnight, and used in the next step without further purification. $^1$H NMR (500 MHz, acetone-d$_6$, δ ppm): 6.5 (s, 1H), 6.1 (s, 1H), 2.1 (s, 3H). $^{19}$F NMR (300 MHz, acetone-d$_6$, δ ppm): −156 (s, 2F), −140.5 (s, 2F).

To a mixture of sodium 2,3,5,6-tetrafluoro-4-(methacryloyloxy)benzene sulfonate (52.0 g, 0.1516 mol) and triphenylsulfonium bromide (42.50 g, 0.1238 mol) was added 300 mL of distilled, de-ionized water and 300 mL of CH$_2$Cl$_2$. The reaction mixture was stirred at room temperature over the weekend. Stirring was stopped and the organic layer was isolated and washed twice with a 1% solution of aqueous ammonium hydroxide (175 mL), and five times with distilled, de-ionized water (250 mL), dried over sodium sulfate, and filtered. A few crystals (about 12.5 mg) of hydroquinone were added and the solvent was completely distilled under reduced pressure to yield the product as a pale, yellow oil. The product was dissolved at 50 wt % in acetonitrile for further use. $^1$H NMR (500 MHz, acetone-d$_6$, δ ppm): 7.8 (m, 15H), 6.5 (s, 1H), 6.1 (s, 1H), 2.1 (s, 3H). $^{19}$F NMR (300 MHz, acetone-d$_6$, δ ppm): −157 (s, 2F), −140 (s, 2F).

Synthesis of (t-butylphenyl)(diphenyl)sulfonium 1,1-difluoro-2-(methacryloyloxy)ethane-1-sulfonate (PAG 1). Triethylammonium 1,1-difluoro-2-(methacryloyl-oxy)ethane-1-sulfonate (5.00 g, 15.1 mmol) and (t-butylphenyl)(diphenyl)sulfonium bromide (6.00 g, 15.0 mmol) were added to a 100 mL round bottom flask, along with 30 mL of dichloromethane and 30 mL of de-ionized water. The mixture was stirred vigorously overnight. Stirring was stopped and the mixture separated into two clear layers; the organic layer was washed once with 30 mL 0.1% aqueous hydrochloric acid and four times with 30 mL of de-ionized water. Hydroquinone (1 mg) was added and dichloromethane was removed by rotary evaporation to yield the product as a colorless, viscous oil (7.2 g, 87% yield). The oil was dissolved to 40 wt % in acetonitrile for further use. $^1$H NMR (500 MHz, acetone-d$_6$) δ 7.9 (m, 14H), 6.1 (s, 1H), 5.7 (s, 1H), 4.7 (m, 2H), 1.9 (s, 3H), 1.3 (s, 9H). $^{19}$F NMR (300 MHz, acetone-d$_6$) δ −115.7 (s, 2F).

Synthesis of (t-butylphenyl)(phenyl)iodonium 1,1-difluoro-2-(methacryloyloxy)ethane-1-sulfonate (PAG 2). Triethylammonium 1,1-difluoro-2-(methacryloyloxy)ethane-1-sulfonate (5.00 g, 15.1 mmol) and (t-butylphenyl)(phenyl)iodonium acetate (5.98 g, 15.1 mmol) were added to a 100 mL round bottom flask, along with 30 mL of dichloromethane and 30 mL of distilled, de-ionized water. The mixture was stirred vigorously overnight, then stopped and the mixture separated into two clear layers; the organic layer was washed once with 30 mL 1% (w/w) aqueous hydrochloric acid and four times with 30 mL of de-ionized water. Hydroquinone (1 mg) was added and dichloromethane removed by rotary evaporation to yield the product as a colorless, viscous oil (7.6 g, 89% yield). The oil was dissolved to 50 wt % in acetonitrile. $^1$H NMR (500 MHz, acetone-d$_6$) δ 8.4 (d, 2H), 8.3 (d, 2H), 7.7 (t, 1H), 7.6 (m, 4H), 6.2 (s, 1H), 5.7 (s, 1H), 4.7 (m, 2H), 1.9 (s, 3H), 1.3 (s, 9H). $^{19}$F NMR (300 MHz, acetone-d$_6$) δ −115.4 (s, 2F).

Synthesis of di(t-butylphenyl)iodonium 2,3,5,6,-tetrafluoro-1-(methacyloyloxy)benzene-4-sulfonate (PAG 3). Sodium 4-hydroxy-2,3,5,6-tetrafluorobenzene sulfonate (50 g, 0.1865 mol) was suspended in 400 mL of trifluoroacetic acid. Methacrylic acid (40 g, 0.4646 mol) was added and the mixture was heated to 70° C. in an oil bath. 75 mL of trifluoroacetic anhydride was added all at once, and the mixture was stirred at 70° C. for two hours. The reaction mixture was cooled to room temperature. A few crystals (about 12.5 mg) of hydroquinone were added, and the solvents were completely distilled under reduced pressure. A paste of the crude product so obtained was dissolved in about 125 mL of acetone and poured slowly into heptane. The precipitated product was collected by filtration, air dried overnight, and used without further purification. $^{19}$F NMR (300 MHz, acetone-$d_6$, δ ppm): −164.40 (s, 2F), −142.4 (s, 2F). $^1$H NMR (500 MHz, acetone-$d_6$, δ ppm): 6.47 (s, 1H), 6.07 (s, 1H), 2.07 (s, 3H).

To a mixture of sodium 2,3,5,6-tetrafluoro-4-(methacryloyloxy)benzene sulfonate (10.0 g, 0.0297 mol) and di-(tert-butylphenyl)iodonium acetate (11.43 g, 0.0253 mol) was added 60 mL of distilled, de-ionized water and 60 mL of $CH_2Cl_2$. The reaction mixture was stirred at room temperature for 16 hours. The organic phase was washed five times with deionized water, dried over sodium sulfate, and filtered. A few crystals (about 12.5 mg) of hydroquinone were added and the solvent removed under reduced pressure to yield the product as white powder. $^1$H NMR (500 MHz, acetone-$d_6$, δ ppm): 8.25 (d, 4H), 7.62 (d, 4H), 6.48 (S, 1H), 6.08 (s, 1H), 2.07 (s, 3H), 1.34 (m, 18H) $^{19}$F NMR (300 MHz, acetone-$d_6$, δ ppm): −139.95 (s, 2F), −156.32 (s, 2F).

Synthesis of Phenyl dibenzothiophenium 1,1-difluoro-2-(methacryloyloxy)ethane-1-sulfonate (PAG 4). Triethylammonium 1,1-difluoro-2-(methacryloyloxy)ethane-1-sulfonate (4.00 g, 12.1 mmol) and phenyl dibenzothiophenium bromide (4.50 g, 31.2 mmol) were added to a 100 mL round bottom flask, along with 30 mL of dichloromethane and 30 mL of distilled, de-ionized water. The mixture was stirred vigorously overnight. Stirring was stopped and the mixture separated into two clear layers; the organic layer was washed twice with 30 mL 1% aqueous hydrochloric acid and five times with 30 mL of distilled, de-ionized water. Hydroquinone (1 mg) was added and dichloromethane was removed by rotary evaporation to yield the product as a solid (3.9 g, 80% yield). $^1$H NMR (500 MHz, $CDCl_3$) δ 8.2 (m, 4H), 7.8 (t, 2H), 7.7 (d, 2H), 7.6 (m, 3H), 7.5 (t, 2H), 6.2 (s, 1H), 5.6 (s, 1H), 4.9 (m, 2H), 1.9 (s, 3H). $^{19}$F NMR (300 MHz, acetone-$d_6$) δ −115.8 (s, 2F).

Synthesis of Triphenylsulfonium 1,1,2,2-tetrafluoro-4-(methacryloyloxy)butane-1-sulfonate (PAG 5). Synthesis of Sodium 4-hydroxy-1,1,2,2-tetrafluorobutane-1-sulfonate. 4-Bromo-3,3,4,4-tetrafluoro-1-butanol (19.92 g, 88.54 mmol) was added to a slurry of $NaHCO_3$ (22.31 g, 265.6 mmol) and $Na_2S_2O_4$ (46.25 g, 265.6 mmol) in 60 mL of acetonitrile and 88 mL of water. The mixture was heated at about 55° C. for two days in a wax bath without stirring. The temperature was increased to about 80° C. and the mixture was stirred. Additional sodium dithionite (17 g) and sodium bicarbonate (15 g) were added. The reaction mixture was allowed to cool to ambient temperature and additional water (100 mL) and acetonitrile (100 mL) were added so that all the solid material dissolved. The layers were separated. The aqueous layer was set aside, and additional sodium dithionite (30 g) and sodium carbonate (38 g) were added to the acetonitrile layer (200 mL) along with about 100 mL of water. The reaction mixture was heated at about 85° C. overnight. The solution was cooled, filtered, combined with the set-aside aqueous layer, and the volatiles were removed on a rotary evaporator. The solid was washed with about 200 mL of ether and dried under vacuum.

The above prepared solid was dissolved in 25 mL of water, cooled down to 0° C. in an ice bath and 50 mL of 50% $H_2O_2$ was added under generation of steam. The reaction mixture was allowed to stir overnight. Additional (20 mL) $H_2O_2$ was added and the stirring was continued. Sodium bisulfite was added until no peroxide remained. The slurry was filtered and the volatiles were removed on a rotary evaporator to give a white solid.

Synthesis of 4-Hydroxy-1,1,2,2-tetrafluorobutane-1-sulfonic acid. The solid from above which contained sodium 4-hydroxy-1,1,2,2-tetrafluorobutane-1-sulfonate was extracted with methanol (100 mL) and filtered. The resulting pale yellow solution was passed through a short column (2.5 cm diameter) which was packed with 7.5 cm of Amberlite 120H acid ion exchange resin to give a light brown solution. Additional methanol was used to flush any remaining sulfonic acid. The volatiles were removed under reduced pressure to give a dark brown oil. The yield was 15.453 g, 77% based on starting 4-bromo-3,3,4,4-tetrafluoro-1-butanol.

Synthesis of 3,3,4,4-tetrafluorobutanesultone. 4-Hydroxy-1,1,2,2-tetrafluoro butane-1-sulfonic acid (6.78 g, 30.0 mmol) was placed in a 50-mL round-bottom flask attached via a V-tube to a Schlenk tube. The system was placed under vacuum and the Schlenk tube was immersed in liquid nitrogen. The flask containing the sulfonic acid was immersed in a hot wax bath and the temperature was gradually raised to about 160° C. The product sultone and water gradually distilled over and froze in the receiver vessel. After thawing, two layers formed. The lower sultone layer was removed by pipette, dried over anhydrous magnesium sulfate, and filtered to give the product as a colorless liquid (3.85 g, 62%). $^1$H NMR (300 MHz, $CD_3CN$) δ: 4.7 (t, 2H), 2.7 (m, 2H). $^{19}$F NMR (300 MHz, $CD_3CN$) δ: −113.3 (m, 2F), −124.4 (s, 2F).

Synthesis of potassium 1,1,2,2-tetrafluoro-4-(methacryloyloxy)butane-1-sulfonate. Methacrylic acid (1.708 g, 19.85 mmol) was added slowly to potassium hydride (1.150 g, 28.66 mmol) in 40 mL of THF. After stiffing overnight, the reaction mixture was filtered and the volatiles removed under reduced pressure. 3,3,4,4-Tetrafluorobutanesultone (3.260 g, 15.66 mmol), methacrylic acid (2.0 mL), and a few crystals of hydroquinone were added to the potassium methacrylate and the mixture heated overnight at 75° C. Acetone (10 mL) was added to the mixture. The solids were collected, washed with acetone, and dried under reduced pressure. The solids were extracted with water, filtered, and the volatiles removed under reduced pressure to give a white crystalline solid (4.10 g, 78.8%). $^1$H NMR (300 MHz, $D_2O$) δ: 6.09 (s, 1H), 5.67 (s, 1H), 4.44 (t, 2H), 2.65 (m, 2H). $^{19}$F NMR (300 MHz, $D_2O$) δ: −112.3 (s, 2F), −117.1 (s, 2F).

Synthesis of Triphenylsulfonium 1,1,2,2-tetrafluoro-4-(methacryloyloxy)butane-1-sulfonate. Potassium 1,1,2,2-tetrafluoro-4-(methacryloyloxy)butane-1-sulfonate (2.00 g, 6.02 mmol) and triphenylsulfonium bromide (2.25 g, 6.57 mmol) were added to a 100 mL round bottom flask, along with 15 mL of dichloromethane and 15 mL of distilled, de-ionized water. The mixture was stirred vigorously for 36 hours. Stirring was stopped and the mixture separated into two clear layers; the organic layer was washed twice with 30 mL 1% aqueous ammonium hydroxide and five times with 30 mL of distilled, de-ionized water. Hydroquinone (1 mg) was added and dichloromethane was removed by rotary evaporation to yield the product as a colorless, viscous oil (2.65 g, 4.76 mmol; 80% yield). The oil was dissolved in acetonitrile (50 wt %) (3.9 g). $^1$H NMR (500 MHz, acetone-$d_6$) δ 8.0 (m, 15H), 6.1 (s, 1H), 5.6 (s, 1H), 4.4 (t, 2H), 3.8 (m, 2H), 1.9 (s, 3H). $^{19}$F NMR (300 MHz, acetone-$d_6$) δ −112.7 (s, 2F), −119.8 (s, 2F).

Synthesis of Phenyl dibenzothiophenium 1,1,2,2-tetrafluoro-4-(methacryloyloxy)butane-1-sulfonate (PAG 6). Potassium 1,1,2,2-tetrafluoro-4-(methacryloyloxy)butane-1-sulfonate, synthesized as described above, (1.91 g, 5.75 mmol) and phenyl dibenzothiophenium bromide (2.14 g, 6.27 mmol) were added to a 100 mL round bottom flask, along with 15 mL of dichloromethane and 15 mL of distilled, de-ionized water. The mixture was stirred vigorously over the weekend. Stirring was stopped and the mixture separated into two clear layers; the organic layer was washed twice with 30 mL 1% aqueous ammonium hydroxide and five times with 30 mL of distilled, de-ionized water. Hydroquinone (1 mg) was added and dichloromethane was removed by rotary evaporation to yield the product as a white solid (2.41 g, 4.35 mmol). $^1$H NMR (500 MHz, acetone-$d_6$) δ 8.0 (m, 15H), 6.1 (s, 1H), 5.6 (s, 1H), 4.4 (t, 2H), 3.8 (m, 2H), 1.9 (s, 3H). $^{19}$F NMR (300 MHz, acetone-$d_6$) δ −112.7 (s, 2F), −119.8 (s, 2F).

Synthesis of tris(4-(2-(2-methoxyethoxy)ethoxy)phenyl)sulfonium 1,1-difluoro-2-(methacryloyloxy)ethanesulfonate (PAG 7). Synthesis of 4,4'-sulfinyldiphenol. A solution of hydrogen peroxide (30 wt % in H$_2$O, 50 mL, 0.382 mol) and triflic anhydride (32.4 mL, 0.191 mmol, 0.5 eq) in ethanol (350 mL) was added dropwise to a solution of 4,4'-thiodiphenol (125 g, 0.573 mol, 1.5 eq) in ethanol (1.25 L) over 4 h. After full addition the reaction mixture was stirred at r.t. for 30 minutes, concentrated in vacuo, diluted with ethyl acetate (1 L) and washed with water (600 mL). The aqueous layer was back extracted with ethyl acetate (3×600 mL), the combined organic layers dried (Na$_2$SO$_4$) and concentrated in vacuo. The crude solid was diluted with methyl tert-butyl ether (1 L) and stirred overnight. The precipitate washed with methyl tert-butyl ether (3×500 mL) and air dried to afford the title compound (100.50 g) as a white solid in quantitative yield. $^1$H NMR (500 MHz, acetone-$d_6$) δ: 8.85-9.05 (brs, 2H), 7.50 (d, J=8.5 Hz, 4H), 6.95 (d, J=8.5 Hz, 4H).

Synthesis of (2-(2-methoxyethoxy)ethoxy)benzene. Phenol (15.0 g, 0.159 mol), potassium carbonate (26.4 g, 0.191 mol, 1.2 eq) and tetramethylethylenediamine (0.92 g, 7.95 mmol, 0.05 eq) were dissolved in DMSO (100 mL) and stirred at r.t. for 30 minutes. Then 1-bromo-2-(2-methoxyethoxy)ethane (30.56 g, 0.166 mol, 1.04 eq) was added, the solution heated to 90° C. for 18 h and cooled to r.t. The reaction mixture was diluted with ethyl acetate (600 mL), washed with 1M potassium hydroxide (3×300 mL), dried (Na$_2$SO$_4$) and concentrated in vacuo to afford the title compound (16.50 g, 52%) as an orange oil. $^1$H NMR (500 MHz, (CD$_3$)$_2$CO) δ: 7.27 (dt, J=8.5 Hz, 1 Hz, 2H), 6.94 (dd, J=8 Hz, 1 Hz, 2H), 6.92 (dt, J=8 Hz, 1 Hz, 1H), 4.12 (t, J=5 Hz, 2H), 3.80 (t, J=5 Hz, 2H), 3.64 (t, J=5 Hz, 2H), 3.50 (t, J=5 Hz, 2H), 3.29 (s, 3H).

Synthesis of 4,4'-sulfinylbis((2-(2-methoxyethoxy)ethoxy)benzene). 4,4'-sulfinyldiphenol (20.0 g, 85.0 mmol), potassium carbonate (26.6 g, 0.192 mol, 2.26 eq) and tetramethylethylenediamine (0.495 g, 4.25 mmol, 0.05 eq) were dissolved in DMSO (100 mL) and stirred at r.t. for 30 minutes. Then 1-bromo-2-(2-methoxyethoxy)ethane (32.67 g, 0.179 mmol, 2.1 eq) was added, the solution heated to 90° C. for 18 h and cooled to r.t. The reaction mixture was diluted with ethyl acetate (600 mL), washed with water (5×500 mL), dried (Na$_2$SO$_4$) and concentrated in vacuo to afford the title compound (33.40 g, 90%) as an orange oil. $^1$H NMR (500 MHz, (CD$_3$)$_2$CO) δ: 7.59 (d, J=8.5 Hz, 4H), 7.07 (d, J=8.5 Hz, 4H), 4.17 (t, J=4.5 Hz, 4H), 3.80 (t, J=5 Hz, 4H), 3.63 (t, J=4.5 Hz, 4H), 3.48 (t, J=4.5 Hz, 4H), 3.28 (s, 6H).

Eaton's Reagent (64 mL) was added dropwise to solution of 4,4'-sulfinylbis((2-(2-methoxyethoxy)ethoxy)benzene) (16.09 g, 36.7 mmol) and (2-(2-methoxyethoxy)ethoxy)benzene (7.20 g, 36.7 mmol, 1 eq.) in dichloromethane (80 mL) over 2 h and stirred at r.t. overnight. The reaction mixture was slowly quenched with the addition of water (500 mL) and extracted with ethyl acetate (5×500 mL). Triethylammonium 1,1-difluoro-2-(methacryloyloxy)ethanesulfonate (14.59 g, 44.04 mmol, 1.2 eq.) was added to the aqueous layer dichloromethane (500 mL) and the resulting biphasic mixture was stirred at room temperature (abbr. r.t.) overnight. The mixture was diluted with water (200 mL), the layers were separated, the aqueous layer extracted with dichloromethane (3×300 mL) and the combined organic layers concentrated in vacuo. The crude oil was dissolved in dichloromethane (800 mL), washed with water (5×500 mL), concentrated in vacuo and residual water removed azeotropically with acetonitrile (2×300 mL) to afford the title compound (26.39 g, 85% yield) as an orange oil. $^1$H NMR (500 MHz, acetone-$d_6$) δ 7.81 (d, J=9 Hz, 4H), 7.35 (d, J=9 Hz, 4H), 6.14-6.16 (m, 1H), 5.67-5.69 (m, 1H), 4.74 (dd, J=15.5, 15 Hz, 2H), 4.30 (t, J=4.5 Hz, 4H), 3.85 (t, J=5 Hz, 4H), 3.65 (t, J=5 Hz, 4H), 3.49 (t, J=4.5 Hz, 4H), 3.28 (s, 9H), 1.94 (m, 3H).

The polymer-bound PAGs used in the examples are as illustrated in Table 1.

TABLE 1

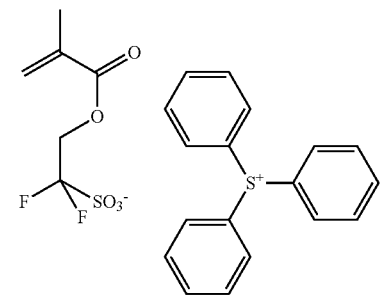

Comparative PAG 1

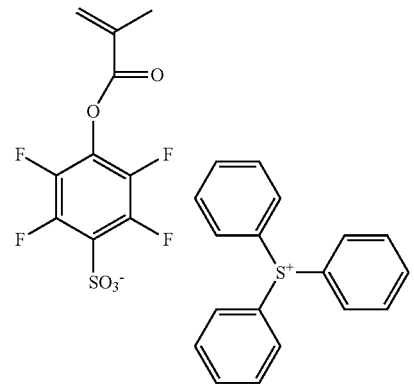

Comparative PAG 2

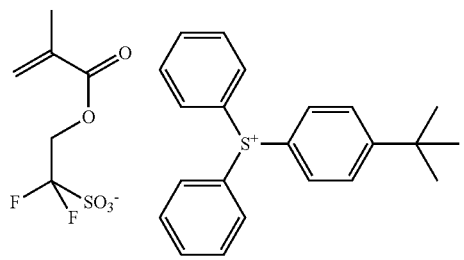

TABLE 1-continued

1

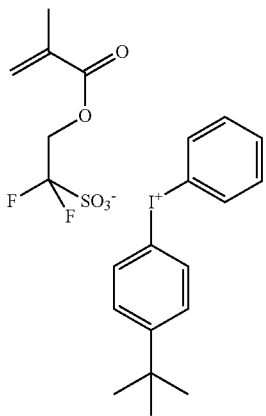

2

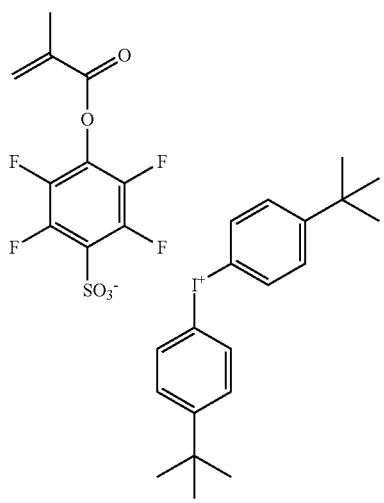

3

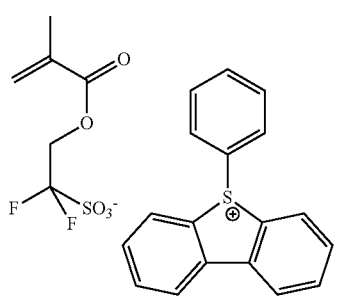

4

TABLE 1-continued

5

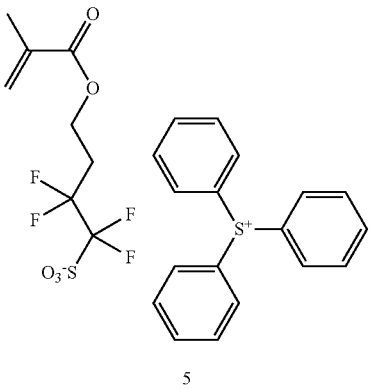

5

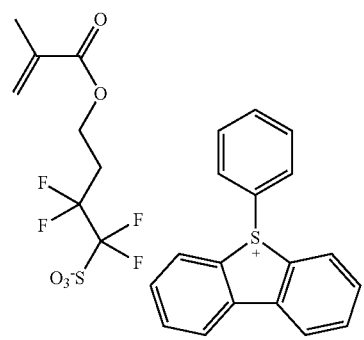

6

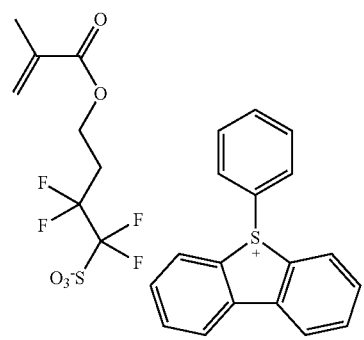

7

Comparative Polymer Example 1A (CPEx. 1A)

Synthesis of Polymer including Comparative PAG 1 (CP1). 2-Phenyl-2-propyl methacrylate (30.16 g, 0.1469 mol), alpha-(gammabutyrolactone)methacrylate (36.54 g, 0.2147 mol), 3,5-bis(1,1,1,3,3,3-hexafluoro-2-hydroxypropan-2-yl)cyclohexyl methacrylate 28.40 g, 56.5 mmol), and triphenylsulfonium 1,1-difluoro-2-(methacryloyloxy)ethane-1-sulfonate (Comparative PAG 1, 16.69 g, 33.9 mmol) were dissolved in 184.14 g of ethyl lactate/cyclohexanone (70/30 v/v). 2,2-Azobis(2,4-dimethyl valeronitrile) (11.24 g, 45.2 mmol) was dissolved in the monomer solution. A small amount of solvent (9.6 g) was introduced to a vessel preheated in an oil bath set to 75° C. and, after 5 min., the monomer solution was fed into the vessel over 4 hours. The reaction mixture was heated for an additional 3.5 hours. The reaction solution was cooled to room temperature and precipitated into 2760 g of agitated isopropyl ether and methanol (95:5 w/w). The resultant polymer was isolated by vacuum filtration and dried in a vacuum oven at 45° C. for 48 hours to yield 97 g (%) of the polymer as a white powder. The dried polymer (90 g) was dissolved and precipitated again into a mixture of agitated isopropyl ether and methanol (95:5 w/w). The resultant re-precipitated polymer was again isolated by vacuum filtration and dried in a vacuum oven at 45° C. for 48 hours to yield 79 g (88%) of the polymer as a white powder. $^{13}$C NMR (500 MHz, acetone-$d_6$) composition 30/46/14/9 mole %, Mw=5,648; Mw/Mn=1.58.

Comparative Polymer Example 1B (CPEx. 1B)

Synthesis of Polymer including Comparative PAG 1. 2-Phenyl-2-propyl methacrylate (8.01 g, 39.2 mmol), alpha-(gammabutyrolactone) methacrylate (9.80 g, 57.2 mmol), 3,5-bis(1,1,1,3,3,3-hexafluoro-2-hydroxypropan-2-yl)cyclohexyl methacrylate (7.54 g, 15.1 mmol), and triphenylsulfonium 1,1-difluoro-2-(methacryloyloxy)ethane-1-sulfonate (Comparative PAG 1, 4.45 g, 9.0 mmol) were dissolved in 94.0 g of acetonitrile/THF (2/1 v/v). 2,2-Azobis(2,4-dimethylvaleronitrile) (1.5 g, 6.0 mmol) was dissolved in the monomer solution. A small amount of solvent (4.6 g) was introduced to a vessel pre-heated in an oil bath set to 67° C. and, after 5 min., the monomer solution was fed into the vessel over 2 hours. The reaction mixture was heated for an additional 2 hours. The reaction solution was cooled to room temperature and precipitated into 959.5 g of agitated isopropyl ether and methanol (90:10 w/w). The resultant polymer was isolated by vacuum filtration and dried in a vacuum oven at 45° C. for 48 hours to yield 15.6 g (53%) of the polymer as a white powder. The dried polymer (11.8 g) was dissolved and precipitated again into a mixture of agitated isopropyl ether and methanol (90:10 w/w). The resultant re-precipitated polymer was again isolated by vacuum filtration and dried in a vacuum oven at 45° C. for 48 hours to yield 10.1 g (86%) of the polymer as a white powder. $^{13}$C NMR (500 MHz, acetone-$d_6$) composition 31/47/13/9 mole %, Mw=7,258; Mw/Mn=1.59.

Comparative Polymer Example 2 (CPEx. 2)

Synthesis of Polymer including Comparative PAG 2. 2-methyl-2-adamantyl methacrylate (27.54 g, 0.1175 mol), alpha-(gammabutyrolactone)methacrylate (22.50 g, 0.1322 mol), 3,5-bis(1,1,1,3,3,3-hexafluoro-2-hydroxypropan-2-yl) cyclohexyl methacrylate (14.70 g, 0.0294 mol), and triphenylsulfonium 2,3,5,6-tetrafluoro-4-(methacryloyloxy)benzene sulfonate, 50 wt % in acetonitrile (Comparative PAG 2, 16.95 g, 0.0147 mol) were dissolved in 211 mL of acetonitrile/THF (2/1 v/v). 2,2-Azobis(2,4-dimethylvaleronitrile) (3.65 g, 0.0147 mol) was dissolved in the monomer solution. Approximately 5-10 mL of the monomer solution was introduced to a vessel pre-heated in an oil bath set to 67° C. and, after 5 min., the rest of the monomer solution was fed into the vessel over 2 hours. The reaction mixture was heated for an additional 2 hours. The reaction solution was cooled to room temperature and precipitated into 2.5 L g of methyl-t-butyl ether The resultant polymer was isolated by vacuum filtration and dried in a vacuum oven at 45° C. for 48 hours to yield 39.6 g (54%) of the polymer as a white powder. $^{13}$C NMR (500 MHz, acetone-$d_6$) composition 37/45/10/8 mole %, Mw=8,360; Mw/Mn=1.75.

Polymer Example 1 (PEx. 1)

Synthesis of Polymer including PAG 1. 2-methyl-2-adamantyl methacrylate (6.86 g, 29.3 mmol), alpha-(gammabutyrolactone)methacrylate (5.60 g, 3.29 mmol), 3,5-bis(1,1,1,3,3,3-hexafluoro-2-hydroxypropan-2-yl)cyclohexyl methacrylate (3.66 g, 7.3 mmol), and t-butylphenyldiphenylsulfonium 1,1-difluoro-2-(methacryloyloxy)ethane-1-sulfonate (PAG 1; 40 wt % solution in acetonitrile, 5.02 g, 3.70 mmol) were dissolved in 54 g of acetonitrile/tetrahydrofuran (2:1 (v/v)). 2,2-Azobis(2,4-dimethylvaleronitrile) (0.91 g, 3.70 mmol) was dissolved in the monomer solution. A small amount (~5 mL) of the monomer solution was introduced to a vessel pre-heated in an oil bath set to 80° C. and, after 5 min., the remainder of the monomer solution was fed into the vessel over 2 hours. The reaction mixture was heated for an additional 2 hours. The reaction solution was cooled to room temperature and precipitated into 0.65 L of agitated methyl t-butyl ether. The resultant polymer was isolated by vacuum filtration and dried in a vacuum oven at 45° C. for 48 hours to yield 10.3 g (55%) of the polymer as a white powder. $^{13}$C NMR (500 MHz, acetone-$d_6$) composition 37/48/9/6 mole %; Mw=8,365, Mw/Mn=1.55.

Polymer Example 2 (PEx. 2)

Synthesis of Polymer including PAG 2. 2-methyl-2-adamantyl methacrylate (6.86 g, 29.3 mmol), alpha-(gammabutyrolactone)methacrylate (5.60 g, 3.29 mmol), 3,5-bis(1,1,1,3,3,3-hexafluoro-2-hydroxypropan-2-yl)cyclohexyl methacrylate (3.66 g, 7.3 mmol), and t-butylphenylphenyliodonium 1,1-difluoro-2-(methacryloyloxy)ethane-1-sulfonate (PAG 2; 50 wt % solution in acetonitrile, 4.15 g, 3.70 mmol) were dissolved in 52 g of acetonitrile/tetrahydrofuran (2:1 (v/v)). 2,2-Azobis(2,4-dimethylvaleronitrile) (0.91 g, 3.70 mmol) was dissolved in the monomer solution. A small amount (~5 mL) of monomer solution was introduced to a vessel pre-heated in an oil bath set to 80° C. and, after 5 min., the remainder of the monomer solution was fed into the vessel over 2 hours. The reaction mixture was heated for an additional 2 hours. The reaction solution was cooled and precipitated into 0.65 L of agitated methyl t-butyl ether. The resultant polymer was isolated by filtration and dried in a vacuum oven at 45° C. for 48 hours to yield 7.6 g, (42%) of the polymer as a white powder. $^{13}$C NMR (500 MHz, acetone-$d_6$) composition 34/47/10/9 mole %; Mw=10,210, Mw/Mn=1.59.

Polymer Example 3 (PEx. 3)

Synthesis of Polymer including PAG 3. Ethyl cyclohexyl methacrylate (6.0 g, 0.0306 mol), gammabutyrolactone (7.6 g, 0.0447 mol), 3,5-bis(1,1,1,3,3,3-hexafluoro-2-hydroxypropan-2-yl)cyclohexyl methacrylate (6.07 g, 0.0118 mol), and di(t-butylphenyl)iodonium 2,3,5,6,-tetrafluoro-1-(methacryloyloxy)benzene-4-sulfonate (PAG 3, 4.98 g, 0.0771 mol) were dissolved in 68 g of THF/acetonitrile (½ v/v). 2,2-Azobis(2,4-dimethylvaleronitrile) (1.17 g, 0.0047 mol) was dissolved in the monomer solution. A small amount of polymerization solvent (~5 g) was introduced to a vessel pre-heated in an oil bath set to 80° C. and, after 5 min., the remainder of the monomer solution was fed into the vessel over 2 hours. The reaction mixture was heated for an additional 2 hours. The reaction solution was cooled to room temperature and precipitated into 1 L of agitated methyl t-butyl ether and Methanol (95/5 v/v). The resultant white powder polymer was isolated by filtration and dried in vacuo at 45° C. for 48 hours (yield 15.5 g, 70%). Mw=15,100 g/mol, Mw/Mn=1.56.

Polymer Example 4 (PEx. 4)

Synthesis of Polymer including PAG 4. 2-Phenyl-2-propyl methacrylate (6.02 g, 29.40 mmol), alpha-(gammabutyrolactone)methacrylate (7.34 g, 42.90 mmol), 3,5-bis(1,1,1,3,3,3-hexafluoro-2-hydroxypropan-2-yl)cyclohexyl methacrylate (5.66 g, 11.30 mmol), and phenyl dibenzothiophenium-1,1-difluoro-2-(methacryloyloxy)ethane-1-sulfonate (PAG 4, 2.36 g, 6.80 mmol) were dissolved in 36.8 g of ethyl lactate/cyclohexanone/tetrahydrofuran (THF) (60:20:20 (w/w)). 2,2-Azobis(2,4-dimethylvaleronitrile) (2.24 g, 9.00 mmol) was dissolved in the monomer solution. A small amount (~5 mL) of monomer solution was introduced to a vessel pre-heated in an oil bath set to 75° C. and, after 5 min., the remainder of the monomer solution was fed into the vessel over 4 hours. The reaction mixture was heated for an additional 3.5 hours. The reaction solution was cooled to room temperature and precipitated into 560 g of agitated isopropyl ether and methanol (95:5 (w/w)). The resultant polymer was isolated by vacuum filtration and dried in a vacuum oven at 45° C. for 48 hours to yield 17 g (76.3%) of the polymer as a white powder. The dried polymer (14 g) was dissolved to 25 wt % solids in THF and precipitated again into a mixture of agitated isopropyl ether and methanol (95:5 (w/w)). The resultant re-precipitated polymer was again isolated by vacuum filtration and dried in a vacuum oven at 45° C. for 48 hours to yield 12 g (86%) of the polymer as a white powder. $^{13}$C NMR (500 MHz, acetone-$d_6$) composition 31/46/14/9 mole %, Mw=4,381; Mw/Mn=1.55.

Polymer Example 5 (PEx. 5)

Synthesis of Polymer including PAG 5. 2-Phenyl-2-propyl methacrylate (3.32 g, 16.25 mmol), alpha-(gammabutyrolactone)methacrylate (4.40 g, 23.75 mmol), 3,5-bis(1,1,1,3,3,3-hexafluoro-2-hydroxypropan-2-yl)cyclohexyl methacrylate (3.13 g, 6.25 mmol), and triphenylsulfonium 1,1,2,2-tetrafluoro-4-(methacryloyloxy)butane-1-sulfonate (PAG 5; 50 wt % solution in acetonitrile; 4.17 g, 3.75 mmol) were dissolved in 16.8 g of ethyl lactate/cyclohexanone (70:30 (v/v)). 2,2-Azobis(2,4-dimethylvaleronitrile) (1.24 g, 3.75 mmol) was dissolved in the monomer solution. A small amount (~5 mL) of monomer solution was introduced to a vessel pre-heated in an oil bath set to 80° C. and, after 5 min., the remainder of the monomer solution was fed into the vessel over 4 hours. The reaction mixture was heated for an additional 2 hours. The reaction solution was cooled to room temperature and precipitated into 1 L of agitated methyl t-butyl ether and 2-propanol (90:10 (v/v)). The resultant polymer was isolated by vacuum filtration and dried in a vacuum oven at 45° C. for 48 hours to yield 7.3 g (58%) of the polymer as a white powder. $^{13}$C NMR (500 MHz, acetone-$d_6$) composition 32/50/10/8 mole %, Mw=6,430; Mw/Mn=1.52.

Polymer Example 6 (PEx. 6)

Synthesis of Polymer including PAG 6. 2-Phenyl-2-propyl methacrylate (3.02 g, 14.63 mmol), alpha-(gammabutyrolactone)methacrylate (3.69 g, 21.38 mmol), 3,5-bis(1,1,1,3,3,3-hexafluoro-2-hydroxypropan-2-yl)cyclohexyl methacrylate (2.86 g, 5.63 mmol), and phenyl dibenzothiophenium 1,1,2,2-tetrafluoro-4-(methacryloyloxy) butane-1-sulfonate (PAG 6, 1.88 g, 3.38 mmol) were dissolved in 16.8 g of ethyl lactate/cyclohexanone (70:30 (v/v)). 2,2-Azobis(2,4-dimethylvaleronitrile) (1.16 g, 4.50 mmol) was dissolved in the monomer solution. A small amount (~5 mL) of monomer solution was introduced to a vessel pre-heated in an oil bath set to 75° C. and, after 5 min., the remainder of the monomer solution was fed into the vessel over 4 hours. The reaction mixture was heated for an additional 3.5 hours. The reaction solution was cooled to room temperature and precipitated into 70 mL of agitated isopropyl ether and methanol (95:5 (w/w)). The resultant polymer was isolated by vacuum filtration and dried in a vacuum oven at 45° C. for 48 hours to yield 6.1 g (53%) of the polymer as a white powder. The dried polymer (5 g) was dissolved to 25 wt % solids in THF and precipitated again into a mixture of agitated isopropyl ether and methanol (95:5 (w/w)). The resultant polymer was isolated by vacuum filtration and dried in a vacuum oven at 45° C. for 48 hours to yield 3.6 g (72%) of the polymer as a white powder. $^{13}$C NMR (500 MHz, acetone-$d_6$) composition 28/20/12.5/9.5 mole %, Mw=4,044; Mw/Mn=1.74.

Polymer Example 7 (PEx. 7)

Synthesis of Polymer including PAG 7. 2-Phenyl-2-propyl methacrylate (0.41 g, mmol), alpha-(gammabutyrolactone) methacrylate (0.34 g, mmol), 3,5-bis(1,1,1,3,3,3-hexafluoro-2-hydroxypropan-2-yl)cyclohexyl methacrylate (0.58 g, mmol), and tris(4-(2-(2-methoxyethoxy)ethoxy)phenyl)sulfonium 1,1-difluoro-2-(methacryloyloxy)ethanesulfonate (PAG 8, 0.65 g, mmol) were dissolved in 14.2 g of ethyl lactate/cyclohexanone (70:30 (v/v)) and introduced to a vessel pre-heated in an oil bath set to 75° C. 2-Phenyl-2-propyl methacrylate (4.64 g, 24.5 mmol), alpha-(gammabutyrolactone)methacrylate (5.80 g, 35.8 mmol), 3,5-bis(1,1,1,3,3,3-hexafluoro-2-hydroxypropan-2-yl)cyclohexyl methacrylate (4.18 g, 9.4 mmol), tris(4-(2-(2-methoxyethoxy)ethoxy)phenyl)sulfonium 1,1-difluoro-2-(methacryloyloxy)ethanesulfonate dissolved at 50 wt % in acetonitrile (PAG 7, 9.90 g, 5.60 mmol), and 2,2-azobis(2,4-dimethylvaleronitrile) (1.86 g, 7.50 mmol) were dissolved in 14.8 g of ethyl lactate/cyclohexanone (70:30 (v/v)). This solution was feed into the reaction vessel over 4 hours. The reaction mixture was heated for an additional 3.5 hours. The reaction solution was cooled to room temperature and precipitated into 370 g of agitated isopropyl ether and methanol (90:10 (w/w)). The resultant polymer was isolated by vacuum filtration and dried in a vacuum oven at 45° C. for 48 hours to yield 8.0 g (39%) of the polymer as a white powder. The dried polymer (7.0 g) was dissolved to 40 wt % solids in THF and precipitated again into a mixture of agitated isopropyl ether and methanol (80:20 (w/w)). The resultant polymer was isolated by vacuum filtration and dried in a vacuum oven at 45° C. for 48 hours to yield 5.8 g (83%) of the polymer as a white powder. $^{13}$C NMR (500 MHz, acetone-$d_6$) composition 38/49/8/5 mole %.

Photoresist preparation and processing. Comparative Formulation Examples 1A, 1B, and 2 and Formulation Examples 1-7, which are positive-tone photoresist compositions of Comparative Polymer Examples 1A, 1B, 2 and Polymer Examples 1-7 (respectively), were prepared to obtain lithographic performance data.

Comparative Formulation Example 1A (CFEx. 1A)

A positive-tone photoresist composition was prepared by combining 1.000 g of Comparative Polymer 1A, 1.000 g of a 1 wt % solution in ethyl lactate (EL) of quencher formed from tetramethylammonium hydroxide and 2-hydroxy benzoic acid, 0.200 g of a 0.5 wt % solution in EL of Omnova PF656 surfactant, 26.100 g of EL solvent and 11.700 g of cyclohexanone solvent (CH), and was filtered (0.2 μm).

Positive-tone photoresist compositions containing Comparative Formulation Example 1B and 2 (CFEx. 1B and 2) and Formulation Examples 1-7 (FEx. 1-7) were prepared in a similar manner, substituting the amounts specified in Table 2. The photoresist formulations of CFEx. 2, FEx. 1, and FEx. 3 PGMEA as solvent instead of cyclohexanone.

TABLE 2

| Formulation Example | Polymer | Polymer soln. in EL (10 wt %) | Quencher soln in EL (1 wt %) | Omnova PF 656 (0.5 wt % in EL) | Omnova PF 656 (1 wt % in EL) | EL | CH | PGMEA |
|---|---|---|---|---|---|---|---|---|
| CFEx 1A | 1.000 g | | 1.000 g | 0.200 g | | 26.100 g | 11.700 g | |
| CFEx 1B | 0.880 g | | 0.180 g | 0.170 g | | 23.500 g | 10.230 g | |
| CFEx 2 | 0.498 | | 0.150 g | | 0.050 g | 19.452 g | | 4.851 g |
| FEx 1 | 1.070 g | | 0.200 g | 0.100 g | | 27.102 g | | 7.701 g |
| FEx 2 | 1.000 g | | 0.200 g | 0.100 g | | 19.302 g | 19.401 g | |
| FEx 3 | 2.760 g | | 0.560 g | 0.280 g | | 77.206 g | | 19.163 g |
| FEx 4 | 0.872 g | | 0.175 g | 0.175 g | | 23.200 g | 10.900 g | |
| FEx 5 | 0.628 g | | 0.139 g | 0.125 g | | 16.800 g | 7.300 g | |
| FEx 6 | 0.870 g | | 0.200 g | 0.180 g | | 23.700 g | 10.000 g | |
| FEx 7 | | 12.560 g | 0.254 g | | 0.131 g | 16.841 g | 12.219 g | |

The above photoresist formulations CFEx. 1A, 1B, and 2, and FEx 1-7 were lithographically processed as follows. The photoresist was spin coated using a TEL ACT-8 (Tokyo Electron) coating track or similar equipment onto a 200 mm silicon wafer having an organic antireflective coating (for 248 nm exposure AR™9, Rohm and Haas Electronic Materials LLC or for 193 nm exposure AR™19, Rohm and Haas Electronic Materials LLC, or an organic underlayer for EUV) and baked at 100-140° C. for 60 or 90 seconds to form a resist film of about 60 nm in thickness. The resulting photoresist layer was exposed through an open-frame mask to KrF excimer laser radiation (248 nm), ArF excimer laser radiation (193 nm), or EUV radiation (eMET, 13.5 nm), post exposure baked at 90-120° C. for 60 seconds and developed with 0.26 N aqueous tetramethylammonium hydroxide developer solution to form a positive-tone photoresist pattern.

Table 3 describes the $E_0$ values obtained for the above photoresist formulations.

TABLE 3

| Formulation Example | PAB ° C./sec | PEB ° C./sec | 248 $E_0$ mJ/cm$^2$ | 193 $E_0$ mJ/cm$^2$ | EUV $E_0$ mJ/cm$^2$ |
|---|---|---|---|---|---|
| CFEx 1A | 100/60 | 90/60 | 10.4 | | 4.9 |
| CFEx 1B | 100/60 | 90/60 | 4.2 | 1 | 3.0 |
| CFEx 2 | 140/90 | 120/60 | 2.7 | | 4.2 |
| FEx 1 | 130/90 | 120/60 | | 1.9 | |
| FEx 2 | 130/90 | 120/60 | | 4.7 | |
| FEx 3 | 140/90 | 90/60 | 17 | | 3.85 |
| FEx 4 | 130/60 | 90/60 | 22 | 7.0 | 3.5 |
| FEx 5 | 100/60 | 90/60 | 2.7 | | |
| FEx 6 | 130/60 | 90/60 | 18 | 5.0 | |
| FEx 7 | 130/90 | 90/60 | 2.4 | 1.1 | 2.1 |

Table 4 describes the molecular weights and estimated relative sizes (based on the volume measurement feature of ChemDraw version 11 (available from CambridgeSoft Inc., substituting a CH for $S^+$ or a $CH_2$ for $I^+$) of the cations included in the polymer-bound PAGs.

TABLE 4

| PAG Example | Onium Cation | Onium Cation MW (g/mol) | Estimated. cation size (cm$^3$/mol) |
|---|---|---|---|
| CPAG 1,2; PAG 5 | TPS | 263.38 | 769.5 |
| PAGs 4, 6 | PDBT | 261.36 | 748.5 |
| PAG 1 | TBPDPS | 319.48 | 982.5 |
| PAG 2 | TBPPI | 337.22 | 760.5 |
| PAG 3 | DTBPI | 393.32 | 973.5 |
| PAG 7 | MEEPS | 617.28 | 1771.5 |

Outgassing of photoresist samples. Photoresist samples of Formulation Examples 3, 4, and 7 were analyzed by residual gas analysis (RGA) at a multiple of 2.3 to 2.5 times an EUV exposure dose-to-clear ($E_0$) value. EUV irradiation on the wafer uses a spot size of ~10 mm$^2$ and power density of ~4 mW/cm$^2$. The RGA test takes place under ultra-high vacuum (~$1.5E^{-8}$ mbar). Further details of the RGA method are similar to that described by Pollentier et. al. in *Proc. SPIE,* 2009, pp. 7271-7246 and *Proc. SPIE,* 2010, p. 7636.

The data, including the $E_0$ data and the RGA results, reported as molecules per square centimeter (molecules/cm$^2$) are shown in Table 5.

TABLE 5

| Formulation Example | Polymer Example | PAG | cation | $E_0$ (EUV) | RGA (molecules/ cm$^2$) | Relative outgassing |
|---|---|---|---|---|---|---|
| CFEx1A | CPEx1A | CP1 | TPS | 4.9 | 7.90E+14 | 1 |
| 4 | 4 | 4 | PDBT | 3.5 | 5.20E+14 | 0.66 |
| 7 | 7 | 7 | MEEPS | 2.1 | 1.50E+14 | 0.19 |
| CFEx2 | CPEx2 | CP2 | TPS | 4.2 | 5.60E+14 | 1 |
| 3 | 3 | 3 | DTBPI | 3.85 | 4.00E+14 | 0.71 |

As seen in the data in Table 4, the PDBT PAG of Polymer Example 4 and the MEEPS PAG of Polymer Example 7 and the DTBPI PAG of Polymer Example 3 show lower levels of outgassing than the triphenylsulfonium-based Comparative PAG 1 and 2.

The Out-Of-Band Radiation performance for Comparative Formulation Example 1B, corresponding to comparative polymer 1B (Comparative PAG 1) and Formulation Examples 4 and 6, corresponding to polymer 4 (PAG 4), and polymer 6 (PAG 6), were determined, and the results provided in Table 6.

TABLE 6

| Formulation Example | Polymer | PAG | $E_0$, DUV (248 nm) in mJ/cm² | $E_0$, 193 (193 nm) in mJ/cm² | $E_0$, EUV (13.4 nm) in mJ/cm² | $E_{0\text{-}EUV}/E_{0\text{-}DUV}$ | $E_{0\text{-}EUV}/E_{0\text{-}193}$ |
|---|---|---|---|---|---|---|---|
| CFEx. 1B | Comparative Polymer 1B | CP1 | 4.2 | 1 | 3 | 0.7 | 3 |
| FEx. 4 | Polymer Example 4 | 4 | 17.4 | 7.0 | 4.0 | 0.2 | 0.6 |
| FEx. 6 | Polymer Example 6 | 6 | 18.0 | 5.0 | 3.6 | 0.2 | 0.7 |

As seen in the above Table 6, each of Polymer Examples 4 and 6 (having PAGs 4 and 6, respectively) provided a lower (i.e., improved) OOB value for EUV wavelengths compared with both 248 nm (DUV) and 193 nm (193) wavelengths for these Formulation Examples, of less than 0.7 overall. Comparative Formulation Example 1B, corresponding to Comparative Polymer 1B (Comparative PAG 1B) exhibited a significantly higher OOB ratio of 3 for $E_{0\text{-}EUV}/E_{0\text{-}193}$.

All ranges disclosed herein are inclusive of the endpoints, and the endpoints are independently combinable with each other. The suffix "(s)" as used herein is intended to include both the singular and the plural of the term that it modifies, thereby including at least one of that term. "Optional" or "optionally" means that the subsequently described event or circumstance can or cannot occur, and that the description includes instances where the event occurs and instances where it does not. As used herein, "combination" is inclusive of blends, mixtures, alloys, or reaction products. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:

1. A copolymer comprising:
a first polymerized unit formed from a compound having the formula

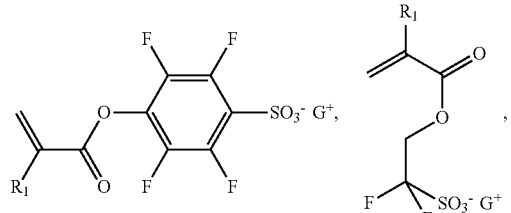

-continued

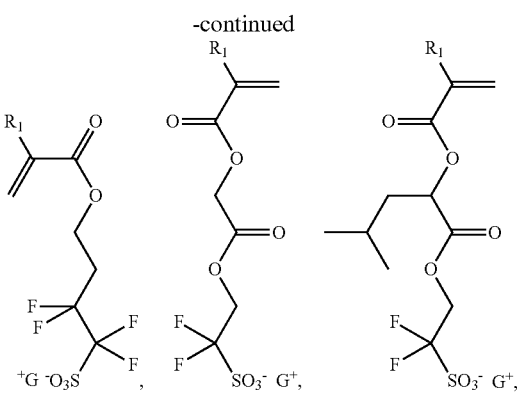

or a combination comprising at least one of the foregoing, where each $R^1$ is independently H, F, $C_{1\text{-}6}$ alkyl, or $C_{1\text{-}6}$ fluoroalkyl, and $G^+$ has formula (VI):

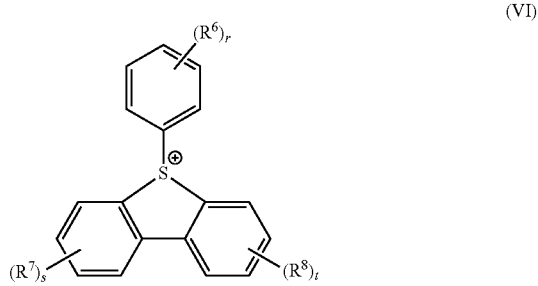

(VI)

wherein $R^6$, $R^7$, and $R^8$ are each independently hydroxy, nitrile, halogen, $C_{1\text{-}10}$ alkyl, $C_{1\text{-}10}$ fluoroalkyl, $C_{1\text{-}10}$ alkoxy, $C_{1\text{-}10}$ fluoroalkoxy, $C_{6\text{-}20}$ aryl, $C_{6\text{-}20}$ fluoroaryl, $C_{6\text{-}20}$ aryloxy, or $C_{6\text{-}20}$ fluoroaryloxy, r is an integer from 0 to 5, and s and t are each independently an integer from 0 to 4;

a second polymerized unit comprising an acid sensitive functional group; and a third polymerized unit comprising a polar group, wherein the third polymerized unit is formed from a polar monomer chosen from

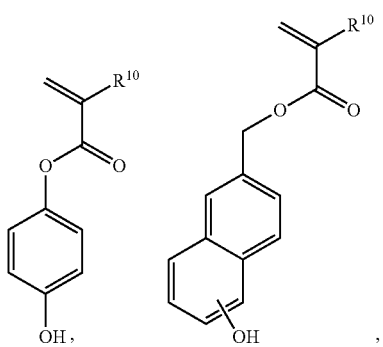

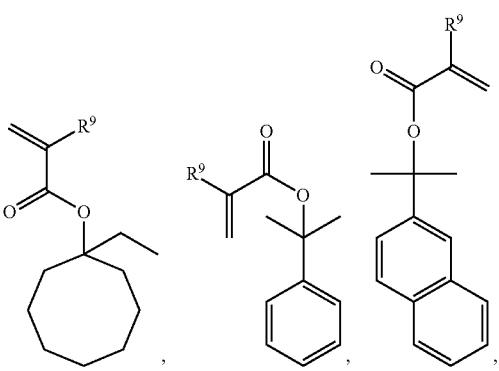

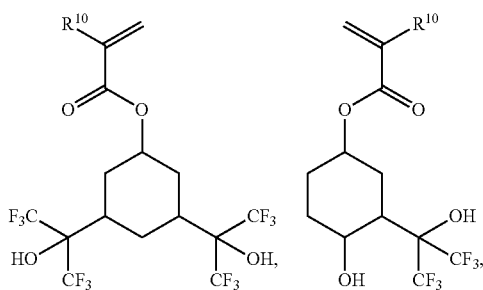

or a combination comprising at least one of the foregoing, wherein $R^{10}$ is H, F, $C_{1-6}$ alkyl, or $C_{1-6}$ fluoroalkyl.

2. The copolymer of claim 1, wherein the second polymerized unit is formed from an acid sensitive monomer comprising:

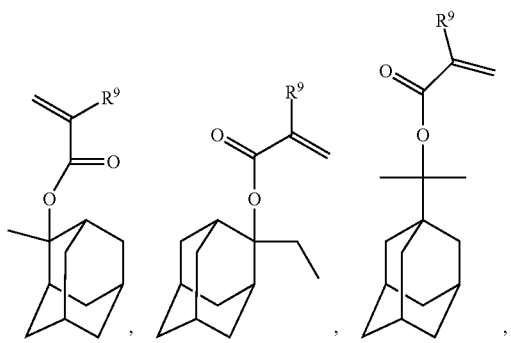

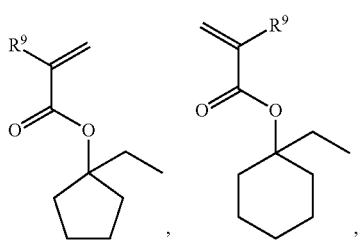

or a combination comprising at least one of the foregoing, wherein $R^9$ is H, F, $C_{1-6}$ alkyl, or $C_{1-6}$ fluoroalkyl.

3. A photoresist composition comprising the copolymer of claim 1.

4. A coated substrate, comprising: (a) a substrate having one or more layers to be patterned on a surface thereof; and (b) a layer of a photoresist composition of claim 3 over the one or more layers to be patterned.

5. A method of forming an electronic device, comprising: (a) applying a layer of a photoresist composition of claim 3 on a substrate; (b) patternwise exposing the photoresist composition layer to activating radiation; and (c) developing the exposed photoresist composition layer to provide a resist relief image.

6. The method of claim 5, wherein the radiation is extreme-ultraviolet or e-beam radiation.

7. The copolymer of claim 1, wherein the second polymerized unit is formed from an acid sensitive monomer comprising

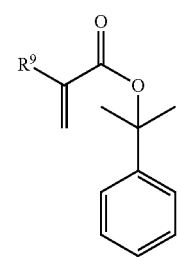

wherein $R^9$ is H, F, $C_{1-6}$ alkyl, or $C_{1-6}$ fluoroalkyl.

8. A copolymer comprising
a first polymerized unit formed from a compound having the formula

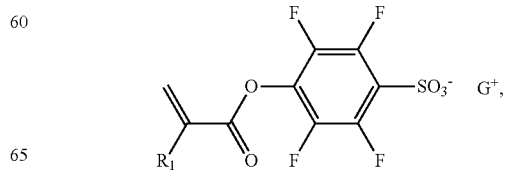

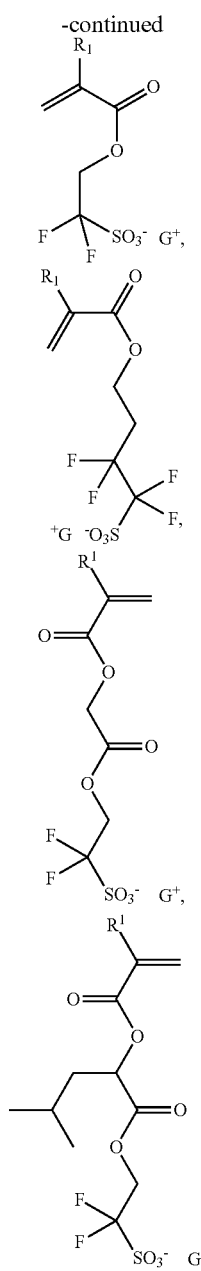

or a combination comprising at least one of the foregoing, where each $R^1$ is independently H, F, $C_{1-6}$ alkyl, or $C_{1-6}$ fluoroalkyl, and $G^+$ has formula (VI)

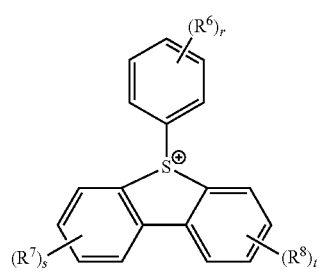
(VI)

wherein $R^6$, $R^7$, and $R^8$ are each independently hydroxy, nitrile, halogen, $C_{1-10}$ alkyl, $C_{1-10}$ fluoroalkyl, $C_{1-10}$ alkoxy, $C_{1-10}$ fluoroalkoxy, $C_{6-20}$ aryl, $C_{6-20}$ fluoroaryl, $C_{6-20}$ aryloxy, or $C_{6-20}$ fluoroaryloxy, r is an integer from 0 to 5, and s and t are each independently an integer from 0 to 4;

a second polymerized unit comprising an acid sensitive functional group; wherein the second polymerized unit is formed from an acid sensitive monomer comprising

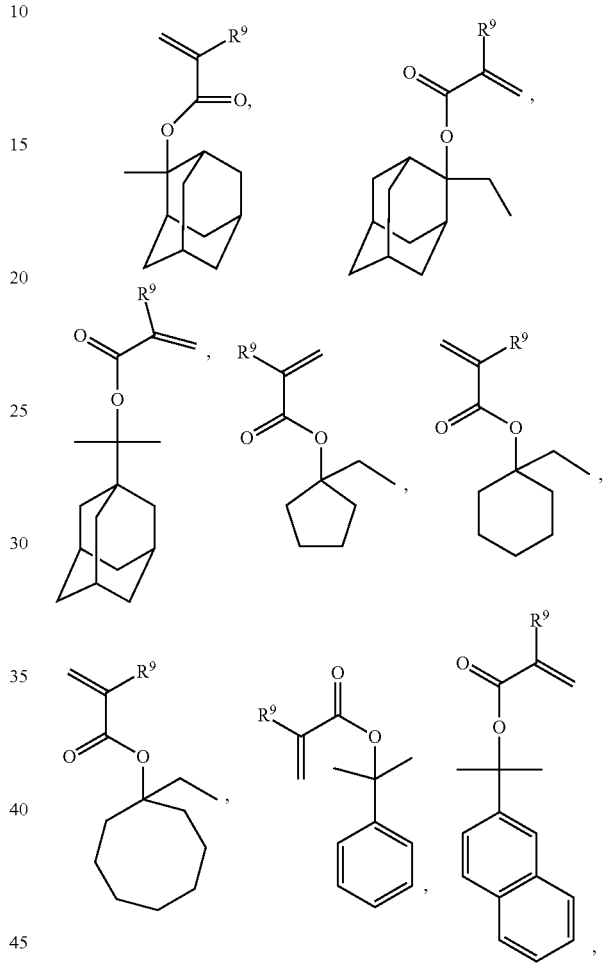

or a combination comprising at least one of the foregoing, wherein $R^9$ is H, F, $C_{1-6}$ alkyl, or $C_{1-6}$ fluoroalkyl; and a third polymerized unit comprising a polar group, wherein the third polymerized unit is formed from the following monomer:

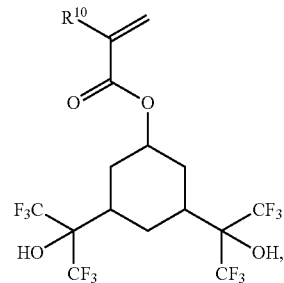

wherein $R^{10}$ is H, F, $C_{1-6}$ alkyl, or $C_{1-6}$ fluoroalkyl.

9. A photoresist composition comprising the copolymer of claim 8.

10. A method of forming an electronic device, comprising: (a) applying a layer of a photoresist composition of claim 9 on a substrate; (b) patternwise exposing the photoresist composition layer to activating radiation; and (c) developing the exposed photoresist composition layer to provide a resist relief image.

* * * * *